United States Patent [19]
Yoshida et al.

[11] Patent Number: 5,602,935
[45] Date of Patent: Feb. 11, 1997

[54] BONE MORPHOMETRIC METHOD USING RADIATION PATTERNS ALONG MEASURING LINES RELATED TO A BONE AXIS AND APPARATUS FOR CARRYING OUT THE SAME

[75] Inventors: Makoto Yoshida, Kobe; Dunhao Chen, Ibaraki, both of Japan

[73] Assignee: Teijin Limited, Osaka, Japan

[21] Appl. No.: 351,282

[22] PCT Filed: Apr. 25, 1994

[86] PCT No.: PCT/JP94/00688

§ 371 Date: Dec. 23, 1994

§ 102(e) Date: Dec. 23, 1994

[87] PCT Pub. No.: WO94/24938

PCT Pub. Date: Nov. 10, 1994

[30] Foreign Application Priority Data

| Apr. 23, 1993 | [JP] | Japan | 5-097629 |
| Apr. 26, 1993 | [JP] | Japan | 5-099411 |
| Apr. 27, 1993 | [JP] | Japan | 5101080 |
| Jun. 29, 1993 | [JP] | Japan | 5-158887 |
| Dec. 17, 1993 | [JP] | Japan | 5-318132 |
| Dec. 17, 1993 | [JP] | Japan | 5-318133 |
| Dec. 17, 1993 | [JP] | Japan | 5-318134 |
| Dec. 17, 1993 | [JP] | Japan | 5-318135 |

[51] Int. Cl.$^6$ ............................................. G06K 9/00
[52] U.S. Cl. ............................................. 382/132; 382/286
[58] Field of Search .................... 382/128, 132, 382/168, 170, 286, 288, 291; 364/413.13; 128/653.1, 659; 378/53, 54

[56] References Cited

U.S. PATENT DOCUMENTS

| 4,903,203 | 2/1990 | Yamashita et al. | 364/413.15 |
| 5,138,553 | 8/1992 | Lanza et al. | 364/413.26 |
| 5,228,068 | 7/1993 | Mazess | 378/54 |
| 5,365,564 | 11/1994 | Yashida et al. | 378/55 |
| 5,426,709 | 6/1995 | Yoshida et al. | 382/132 |

FOREIGN PATENT DOCUMENTS

| 62-183748 | 8/1987 | Japan | A61B 6/00 |
| 4-84939 | 3/1992 | Japan | A61B 6/00 |
| 5-95940 | 4/1993 | Japan | A61B 6/00 |

OTHER PUBLICATIONS

"Assessment of bone density in the distal radius with computer assisted X–ray densitometry (CXD)," part of the program summary of The Second Japan Osteoporosis Research Conference by the Japan Osteoporosis Foundation on Nov. 19 and 20, 1993. Program publish on Oct. 30, 1993, Seo et al. p. 105.

"Single Photon Absorptiometry," *Bone Mineral Measurement and Osteoporosis*, K. Yamamoto, pp. 55–63. (no date).

"A Computer–Assisted Method for the Study of the Trabecular Bone of the Distal Radius on Conventional Radiographs," *Journal of Digital Imaging*, by Donatella Trippi et al, vol. 6, No. 2 (May) 1993; 140–147.

*Primary Examiner*—Andrew Johns
*Attorney, Agent, or Firm*—Sughrue, Mion, Zinn, Macpeak & Seas

[57] ABSTRACT

The present invention relates to a bone morphometric method using a radiograph capable of measuring a sample bone with enhanced accuracy, which comprises, inter alia, determining a bone axis by specifying two points on the head of the sample bone and two points on the shaft of the sample bone in a region of interest in the radiograph, and interconnecting the middle point on the line connecting the former two points and the middle point on the line connecting the latter two points. The present invention is also directed to a bone morphometric apparatus for carrying out the bone morphometric method.

23 Claims, 25 Drawing Sheets

CHANGE OF BMD (%)

SECOND METACARPUS $$BMD = \frac{S}{D/3}$$

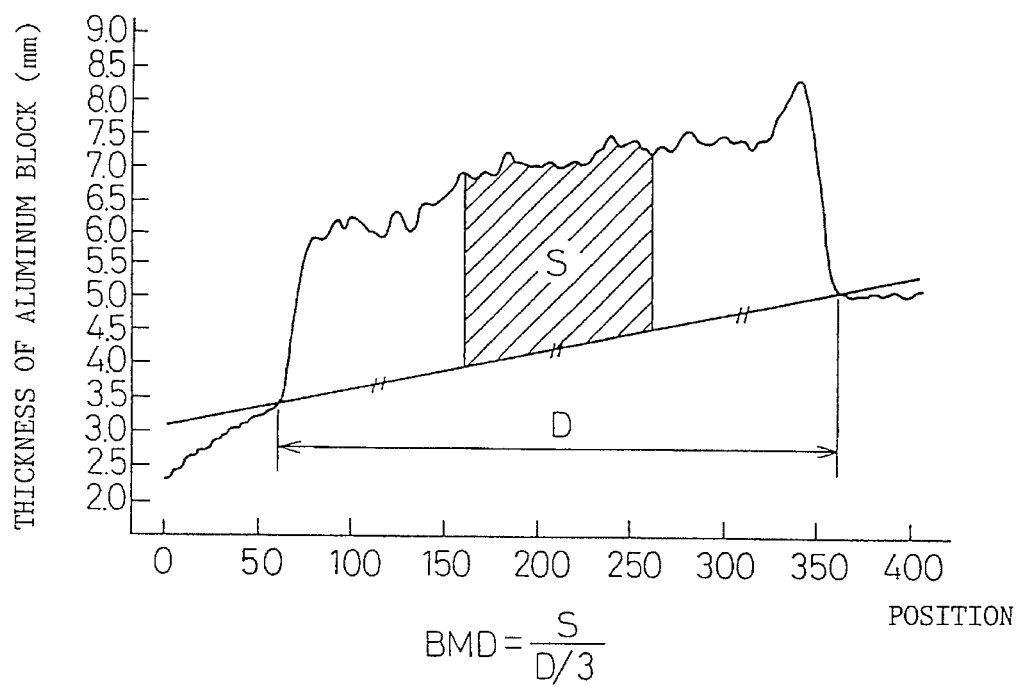

Fig.27
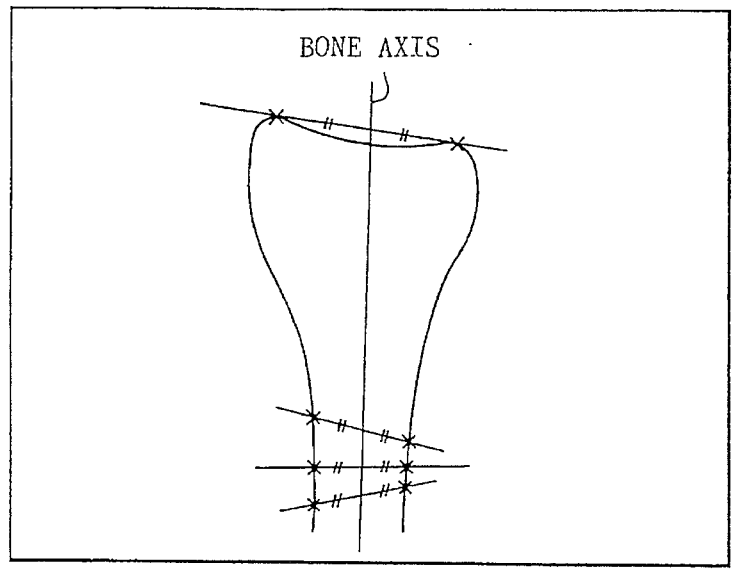
DIRECTION OF RADIATION
Fig.28A
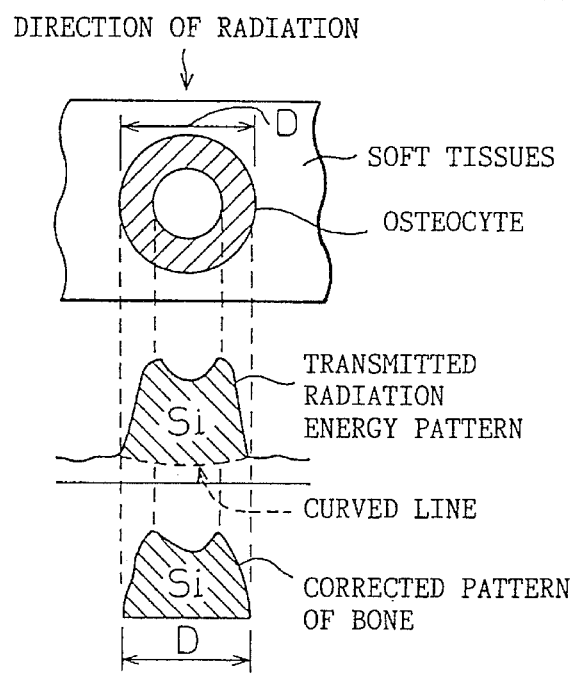
SOFT TISSUES
OSTEOCYTE
Fig.28B
TRANSMITTED RADIATION ENERGY PATTERN
CURVED LINE
Fig.28C
CORRECTED PATTERN OF BONE
Fig.28D
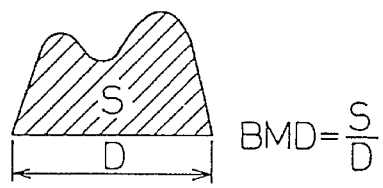
$BMD = \dfrac{S}{D}$
Fig.28E
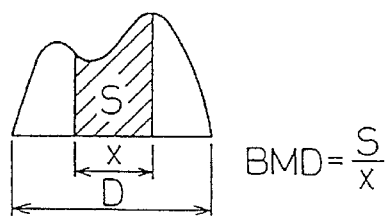
$BMD = \dfrac{S}{X}$

BONE MORPHOMETRIC METHOD USING RADIATION PATTERNS ALONG MEASURING LINES RELATED TO A BONE AXIS AND APPARATUS FOR CARRYING OUT THE SAME

TECHNICAL FIELD

The present invention relates to a bone morphometric method and a bone morphometric apparatus. More specifically, the present invention provides a bone morphometric method capable of measuring the pattern of the quantity of radiation transmitted through a sample bone, among bones suitable for measurement including a radius and a metacarpus, obtained from an image based on an image formed by irradiating the sample bone with radiation and measuring the transmitted radiation and of performing rational and accurate assay of the sample bone in terms of bone assaying parameters, particularly, by cancellate bone assaying parameters, and a bone morphometric apparatus for carrying out the same bone morphometric method.

BACKGROUND ART

The morphologies of human bones are measured to assay the growth and aging of bones, to diagnose and determine the degree of progress of bone diseases such as osteoporosis and osteomalacia, or to confirm a therapeutic effect.

Human bones are classified into cortical bones and cancellate bones. Cortical bones have dense bone structures having the shapes of pipes. Representative cortical bones are the shafts of the long tubular bones of the extremities.

Cancellate bones have mesh structures of osteocytes and are the epiphyses of long tubular bones, vertebrae, carpal bones, heel bones, anklebones, tarsi and such. Osteocytes of cancellate bones, as compared with those in cortical bones, have large areas in contact with soft tissues including blood vessels. Therefore, the progress of metabolism of cancellate bones is rapid and hence the progress of bone diseases in cancellate bones or changes in the state of cancellate bones caused by therapy are rapid.

MD, photon absorptiometry and radioscopy are used in generally known bone morphometric methods. MD measures density distribution in a roentgenogram of a sample bone, produced on an x-ray film by irradiating a sample bone with X-rays, by a microdensitometer (Kotsu Taisha, Vol. 13, 00. 187–195 (1980) and Kotsu Taisha, Vol. 14, pp. 91–104 (1981)), photon absorptiometry irradiates a sample bone with gamma rays and measures the quantity of transmitted gamma rays with a detector, and radioscopy irradiates a sample bone with X-rays and measures the quantity of transmitted X-rays with a detector.

MD is easily applicable to bone measurement and has progressively become prevalent because MD uses x-ray photographs that can be readily produced by the widespread x-ray photographic apparatuses which are widely used for diagnosing bone fractures.

These known bone morphometric methods, however, require drawing work for specifying a reference measuring line and a plurality of ROIs (regions of interest) near the reference measuring line on the x-ray photograph of a sample bone and it is difficult for even the same examiner to specify the same reference measuring line in examining the change in the sample bone and, consequently, accurate observation of the change in the sample bone cannot be achieved; that is, the ROI of the same sample bone cannot be accurately reproduced on each of a plurality of x-ray photographs of the same sample bone and, particularly with cancellate bones, the BMD (bone mineral density) varies widely with the variation of ROIs.

For example, in the SPA method (single photon absorptiometric method), in which a portion at a position along the bone equal to 1/6 of the length of the radius or 1/10 of the length of the ulna is measured, an operator measures the length of the radius or the ulna with a measure, puts a mark on the skin at a position corresponding to a measuring part, and then adjusts the forearm so that the forearm extends perpendicularly to a scanning direction in specifying a region of interest hereinafter referred to as an ROI ("Kotsu Mineraru Sokutei to Kotsu Soshyo Shyo", Medical Review K. K. (1989)). Therefore, the accurate reproduction of the ROI cannot be achieved due to errors in measuring the length of the radius or the ulna with a measure, and errors in determining the position to be marked, and this procedure needs a comparatively long time. Similarly, the drawing work for specifying an ROI on an x-ray film specifies a reference line by measuring the length of the radius or the ulna, and drawing a perpendicular on a center line connecting the head of the measured bone and the epiphysis of the same at a position at a distance equal to the measured length of the radius or the ulna, and uses the perpendicular as a reference line to specify an ROI. Errors in specifying the ROI entails an increase in the CV (Coefficient of Variance). The drawing work requiring a comparatively long time has been an obstacle to quick measurement.

In principle, because the patterns of the quantity of transmitted radiation obtained by the known bone morphometric methods include mixed information about the cortical and the cancellate bones, the known bone morphometric methods are unable to measure a region mostly including cortical bone and a region mostly including cancellate bone separately.

The inventors of the present invention have previously proposed, in Japanese Unexamined Patent Publication (Kokai) No. 4-84939, a bone morphometric method that reads an x-ray image of a sample bone formed on an x-ray film, comprising a process of obtaining a first smoothed pattern by obtaining density patterns of the sample bone along a plurality of substantially parallel measuring lines in a selected region of the input image and smoothing the plurality of density patterns at corresponding positions, and, if necessary, a process of obtaining a second smoothed pattern by smoothing the values of a plurality of nearby points along the measuring pattern in the first smoothed pattern.

However, when measuring the BMD of a cancellate bone by the conventional techniques, the measured BMD of the bone varies in a wide range due to the dislocation of image read lines for measurement for some kind of sample bones and for some measuring portions as shown in FIG. 1, which makes repeatable bone measurements difficult.

The conventional techniques are intended principally to measure the long tubular bones, such as the middle portion of the second metacarpus. The conventional technique determines the axis of a sample bone, i.e., the center axis of the sample bone, measures the quantity of light transmitted, through the X-ray film, along a plurality of measuring lines perpendicular to the bone axis and spaced at fixed intervals to obtain a light quantity pattern, and smoothes the pattern of the quantity of transmitted light with respect to a direction parallel to the bone axis to compose a pattern to improve repeatability. In the case of the long tubular bone, since the pattern along the bone axis shifts, i.e., the width of the bone changes, only a small amount, the change of the BMD (bone mineral density) attributable to a distortion of the pattern when composing the pattern is small. However, a shift in a pattern of the quantity of transmitted light along the bone axis is large when measuring a cancellate bone such as the end portion of the radius. Therefore, when the pattern covers for a wide area and includes a plurality of measuring lines, the pattern can be distorted greatly and the BMD may not be accurately determined (FIGS. 19A and 10B).

The known bone morphometric methods are applied, in most cases, to the measurement of a typical cortical bone which is isolated from other bones and then the measurement is scarcely affected by the nearby bones and cartilage.

However, when another bone (such as an ulna) exists near the sample bone (such as a radius) and the measurement is liable to be affected by the nearby bone as shown in FIG. 27 and when the sample bone has much cancellate bone as shown in FIG. 28, the transmitted radiation forms a complicated BMD pattern and the measurement is liable to be affected by other bones and soft tissues. Therefore, the known bone morphometric methods are unable to measure the sample bone accurately when the BMD pattern of the transmitted radiation is complicated.

DISCLOSURE OF THE INVENTION

In view of the conventional techniques, it is a principal object of the present invention to provide an improved bone morphometric method by incorporating improvements into the conventional bone morphometric methods and to provide a bone morphometric apparatus for carrying out the improved bone morphometric method.

Another object of the present invention is to provide a bone morphometric method capable of discriminating between a region mostly containing cortical bone and a region mostly containing cancellate bone and of accurately measuring a sample bone, and a bone morphometric apparatus for carrying out the bone morphometric method.

A further object of the present invention is to provide an improved bone morphometric method capable of accurately measuring a cancellate bone with high repeatability, and a bone morphometric apparatus for carrying out the improved bone morphometric method.

A still further object of the present invention is to provide an improved bone morphometric method capable of accurately measuring a sample bone even if the sample bone has a complicated BMD pattern of the transmitted radiation, and a bone morphometric apparatus for carrying out the improved bone morphometric method.

The inventors of the present invention have made intensive studies to improve the repeatability of setting an ROI on an image of a bone and have improved the repeatability of setting an ROI and have curtailed time necessary for measurement by marking two protruding points at the head of the radius of a cancellate bone and, marking two points on the shaft with marks, representing the bone axis by a line interconnecting the middle point between the two marks in the head of the bone and the middle point between the two marks on the shaft, drawing a perpendicular on the bone axis at the middle point between the two marks in the head of the bone or at a point at a given distance from one of the two marks in the head of the bone, and automatically specifying the perpendicular as a reference measuring line by a computer means. The present invention has been made through a finding that it is preferable to use a value based on the length of the metacarpus as the given distance because an x-ray photograph formed on an x-ray film includes both an image of the radius and of the metacarpus.

The present invention provides a bone morphometric method which measures a sample bone by using a radiograph of the sample bone, comprising: (i) a step of determining a bone axis by specifying two points on the head of the bone and two points on the shaft in a region of interest in the radiograph of the sample bone and connecting the middle point between the former two points and the middle point between the latter two points, (ii) a step of specifying a reference measuring line perpendicular to the bone axis at a given distance along the bone axis from anyone of the two points in the head of the bone and the middle point between the two points, (iii) a step of determining a pattern of the quantity of radiation transmitted through the sample bone along the reference measuring line, or one or a plurality of measuring lines extending near the reference measuring line and (iv) a step of measuring the sample bone by processing the pattern by arithmetic operations.

The bone morphometric method in accordance with the present invention may be such that the sample bone is a radius, and the unit of the given distance is the length of a metacarpus.

The bone morphometric method in accordance with the present invention may be such that the image is obtained by detecting the quantity of transmitted light determined by irradiating a radiograph including an image of the sample bone and an image of a standard matter having gradate thickness with light and measuring the light transmitted through the radiograph, and the pattern is a density pattern of the bone based on the relation between the thickness of the standard matter and the quantity of transmitted light.

The present invention provides a bone morphometric apparatus, which uses a radiograph of a sample bone for measuring the sample bone, comprising (i) a bone axis determining means for determining a bone axis by specifying two points on the head of the sample bone and two points on the shaft of the sample bone, and connecting the middle point between the former two points and the middle point between the latter two points, (ii) a reference measuring line setting means for setting a reference measuring line perpendicularly intersecting the bone axis at a point at a distance along the bone axis from anyone of the two points on the head of the sample bone and the middle point between the same two points, (iii) a pattern forming means for forming a pattern of the quantity of radiation transmitted through the sample bone along the reference measuring line, or a single measuring line or a plurality of measuring lines near the reference measuring line, and (iv) a measuring means for measuring the sample bone by processing the pattern by predetermined arithmetic operations.

The bone morphometric apparatus in accordance with the present invention includes a bone morphometric apparatus wherein the sample bone is a radius, a means for measuring the length of a metacarpus measures the length of the metacarpus and uses the measured length of the metacarpus.

The bone morphometric apparatus in accordance with the present invention further includes a bone morphometric apparatus wherein the image input means is an image reading means that irradiates a roentgenogram of the sample bone formed on an x-ray film together with a radiograph of a standard matter having gradate thickness with light and detects the quantity of transmitted light, and converting means converts the density pattern of the roentgenogram of the sample bone into values expressed by the thickness of the standard matter on the basis of the relation between the thickness of the standard matter and the quantity of transmitted light determined by irradiating the roentgenogram with light and measuring the light transmitted through the roentgenogram.

The inventors of the present invention made intensive studies on methods of objectively and qualitatively assaying cortical bones and cancellate bones and have found that a region mostly containing cortical bone and a region mostly containing cancellate bone can be discriminated from each other and can be accurately measured by processing a pattern of the quantity of transmitted radiation by arithmetic operations only in a given region determined on the basis of the bone width of a sample bone in a pattern of the quantity of transmitted radiation obtained from an image of a transmission radiograph produced by irradiating the sample bone with radiation. The present invention has been made on the basis of the finding of the studies.

The present invention provides a bone morphometric method, which measures a sample bone by using a radiograph of the sample bone, comprising steps of measuring a pattern of the quantity of radiation transmitted through the sample bone along a single measuring line or a plurality of measuring lines in a selected portion of the image of the sample bone, and processing only the pattern of a local region determined beforehand on the basis of the bone width of the sample bone by arithmetic operations.

The bone morphometric method includes a bone morphometric method such that the local region determined beforehand on the basis of the bone width of the sample bone is a region corresponding to a cancellate bone and equally extending on the opposite sides of the middle of the bone width of the sample bone. A desirable local region is, for example, a region corresponding to the cancellate bone in the range of ⅓ to ½ of the width of the distal end of the radius equally extending on the opposite sides of the middle of the bone width.

The bone morphometric method includes a bone morphometric method such that the image is obtained by detecting the quantity of transmitted light determined by irradiating a radiograph including an image of the sample bone and an image of a standard matter having gradate thickness with light and measuring the light transmitted through the radiograph, and the step of processing the pattern by arithmetic operations for bone measurement converts the pattern into values expressed by the thickness of the standard matter on the basis of the relation between the thickness of the standard block determined from the roentgenogram formed on the x-ray film and the quantity of the transmitted light.

The present invention provides a bone morphometric apparatus, which uses a radiograph of a sample bone for bone measurement, comprising a pattern measuring means for measuring a pattern of the quantity of radiation transmitted through the sample bone along a single measuring line or a plurality of measuring lines in a selected region of the radiograph of the sample bone, and a measuring means for processing only a portion of the pattern corresponding to a local region determined beforehand on the basis of the width of the sample bone by arithmetic operations.

The bone morphometric apparatus in accordance with the present invention includes a bone morphometric apparatus characterized by a region setting means for setting the predetermined region in the pattern of the quantity of transmitted radiation in a region mostly including cancellate bone.

Furthermore, the bone morphometric apparatus in accordance with the present invention includes a bone morphometric apparatus, wherein the image input means is an image reading means for reading an image by detecting the quantity of light transmitted through a radiograph including an image of the sample bone and an image of a standard matter having gradate thickness when the radiograph is irradiated with light, and a converting means converts the plurality of smoothed patterns, i.e., patterns each obtained by composing patterns of the quantity of transmitted light measured along a plurality of parallel measuring lines spaced at equal intervals in a single pattern of the quantity of transmitted light in a direction perpendicular to the measuring lines and by calculating the moving mean of the composed pattern, into values expressed in terms of the thickness of the standard matter.

The inventors of the present invention made intensive studies to enable accurate measurement of cancellate bones with high repeatability and found that the BMD can be accurately measured with high repeatability by integrating a plurality of density patterns in a single smoothed density pattern in a narrow region, determining bone parameters from the smoothed density pattern, repeating the same procedure for other narrow regions, and combining the bone parameters for the narrow regions to obtain average bone parameters for a wide region, and have made the present invention. When necessary, the bone parameters are compared with given standard values to eliminate abnormal bone parameters and the normal bone parameters are averaged.

The present invention provides a bone morphometric method, which measures a sample bone using a radiograph of the sample bone, comprising:

(1) obtaining a plurality of smoothed patterns by measuring patterns of the quantity of transmitted radiation along a plurality of substantially different given lines to obtain patterns of the quantity of transmitted radiation, and repeatedly smoothing the individual patterns by using some of the patterns;

(2) obtaining a plurality of groups of parameters for a bone measurement by processing the plurality of smoothed patterns by predetermined arithmetic operations; and (3) processing the plurality of groups of parameters under a given conditions for measuring the sample bone.

The bone morphometric method in accordance with the present invention includes a bone morphometric method wherein the process for processing the plurality of groups of parameters under a given condition comprises steps of comparing the individual groups of parameters with given standard values, eliminating the groups of parameters deviating from given standard values, and calculating the mean values of the parameters of the remaining groups of parameters; a bone morphometric method wherein the standard values relate to the bone width in the smoothed pattern; and a bone morphometric method wherein the image is read by detecting the quantity of transmitted light determined by irradiating a radiograph including an image of the sample bone and an image of a standard matter having gradate thickness with light and measuring the light transmitted through the radiograph, the pattern of the quantity of transmitted radiations is a density pattern of the sample bone, and the predetermined arithmetic operations have a step of converting the smoothed pattern into values expressed by the thickness of the standard matter on the basis of the relation between the thickness of the standard matter determined from the radiograph and the quantity of transmitted light.

The present invention provides a bone morphometric apparatus, which uses a radiograph of a sample bone for measuring the sample bone, comprising:

(1) a means for obtaining a plurality of smoothed patterns by measuring patterns of the quantity of transmitted radiations along a plurality of substantially different given lines in a selected region in the image of the sample bone to obtain groups of patterns of the quantity of transmitted radiations and repeating a smoothing process for smoothing the individual groups of patterns by using some of the groups of patterns;

(2) a means for obtaining a plurality of groups of parameters for bone measurement by processing the plurality of smoothed patterns by predetermined arithmetic operations; and (3) a means for measuring the sample bone by processing the plurality of groups of parameters under a given condition.

The bone morphometric apparatus in accordance with the present invention includes a bone morphometric apparatus wherein the means for measuring the sample bone has a means for calculating the mean values of the given standard values and those of the parameters of the groups of parameters.

The present invention includes a bone morphometric apparatus that carries out a step of using the bone width of the smoothed pattern in a region of interest as the standard value.

The present invention includes a bone morphometric apparatus, in which the image input means reads an image by detecting the quantity of transmitted light determined by irradiating a radiograph having an image of a sample bone and an image of a standard matter having gradate thickness with light and measuring the light transmitted through the radiograph, comprising:

(1) a means for obtaining a plurality of smoothed patterns by obtaining a plurality of density patterns of the sample bone along a plurality of substantially different given measuring lines near the sample bone and smoothing the plurality of density patterns at corresponding positions;

(2) a means for obtaining a plurality of groups of parameters necessary for bone measurement by converting the plurality of smoothed patterns into values expressed by the thickness of the standard matter on the basis of the relation between the thickness of the standard matter obtained from the radiograph and the quantity of the transmitted light to obtain a converted smoothed pattern, and processing the plurality of converted smoothed patterns by arithmetic operations; and (3) a means for measuring the sample bone by processing the plurality of groups of bone parameters under give conditions.

The inventors of the present invention found through intensive studies that a sample bone can be correctly and accurately measured by normalizing the values of a pattern of BMD as required, based on the quantity of transmitted radiations obtained from the image of the quantity of radiation transmitted through a sample, determining a plurality of proposed boundary points between the region of a sample bone and a region including only soft tissues by using the product of the values of a pattern of BMD, and a difference of a second order and a difference of a first order, and/or the difference of second order, selecting the proposed boundary points meeting a given condition from among the proposed boundary points, and repeating a process in a range according to the pattern when necessary until a linear regression line meets a given condition, and have made the present invention.

The present invention provides (i) a bone morphometric method comprising: an image input step of obtaining an image based on the quantity of transmitted radiation determined by irradiating a sample bone with radiation and measuring the radiation transmitted through the sample bone; a step of determining the quantity of radiation transmitted through a selected region along measuring lines in the selected region of an input image, a step of determining two boundary points between soft tissues and bony tissues at the opposite ends of the sample bone; a step of determining a corrected pattern of the quantity of radiation transmitted through the sample bone proper by subtracting a region relating to the quantity of transmitted radiations transmitted through the soft tissues approximated by a line interconnecting the two boundary points from the pattern; and a step of processing the corrected pattern to measure the sample bone. The present invention also provides (ii) a bone morphometric method according to the bone morphometric method (i), wherein the a step of determining at least one of the two boundary points between the soft tissues and the bony tissues at the opposite ends of the sample bone in the pattern determines an inside first neighborhood point in the pattern, determines a first regression line in a given range (2) by skipping by a given range (1) from the first neighborhood point toward the center of the sample bone, determines an outside first regression line in a given range (4) by skipping by a given range (3) from the first neighborhood point away from the center of the sample bone, sets a second neighborhood point at the intersection of the inside first regression line and the outside first regression line, and repeats the foregoing procedure until a new neighborhood point meeting the given conditions, is determined.

The present invention also provides (iii) a bone morphometric method according to the bone morphometric method (ii), wherein a step of determining the first neighborhood point uses a second difference in the pattern and/or the product of a second difference and a first difference.

The present invention also provides (iv) a bone morphometric apparatus comprising: an image input means for providing an image based on the quantity of transmitted radiation determined by irradiating a sample bone with radiations and measuring the radiation transmitted through the sample bone; a pattern determining means for determining a pattern of the quantity of radiation transmitted through a selected region along a measuring line in the selected region in the input image; a corrected pattern determining means for determining a corrected pattern of the quantity of radiation transmitted through the sample bone proper by setting two boundary points between soft tissues and the bone at each of the opposite ends of the sample bone, and subtracting a region relating to the quantity of transmitted radiation corresponding to the soft tissues approximated by a line interconnecting the middle point between the two boundary points at one end of the sample bone and the middle point between the two boundary points at the other end of the sample bone; and an arithmetic means for processing the corrected pattern by arithmetic operations for bone measurement.

Preferred modes of the bone morphometric methods will be enumerated below.

A first preferred mode (v) is any one of the bone morphometric methods (i) to (iii), wherein the step of determining the boundary points between the soft tissues and the bone tissues at the opposite ends of the sample bone comprises determining a first neighborhood point in the pattern by a predetermined method, determining an inside first regression line in a predetermined range (2) skipping a predetermined range (1) toward the center of the sample bone, skipping a predetermined range (3) from the first neighborhood point away from the center of the sample bone, calculating the mean value of the pattern of the quantity of transmitted radiation in a predetermined range (4) instead of determining the first regression line if the range (4) does not meet a given condition, determining a straight line of a fixed quantity of radiations passing the mean value, employing the intersection of the straight lines as a new neighborhood point, and repeating the foregoing procedure until the new neighborhood point meets a given condition.

A second preferred mode (vi) is any one of the bone morphometric methods (i) to (iii) and (v), wherein the step of determining the first neighborhood point comprises determining a plurality of proposed points by using the product of a second difference and a first difference, and/or the second difference, and selecting a point meeting a given condition from among the plurality of proposed points.

A third preferred mode ((vii) is the bone morphometric method (ii) or (v), wherein a range between a first neighborhood point and a neighborhood point where the gradient from the first neighborhood point toward the center of the sample bone changes greatly is used as the predetermined range (2), and a range between the first neighborhood point and a neighborhood point where the gradient from a point away from the center of the sample bone meets the given condition (1) changes greatly, is used as the predetermined range (4).

A fourth preferred mode (viii) is the bone morphometric method (vii) wherein a condition, that the product of the first difference and the second difference is smaller than a given value, is used as the given condition.

A fifth preferred mode (ix) is the bone morphometric method (i) wherein the process is carried out after normalizing the values of the pattern of the quantity of transmitted radiation using the representative of the pattern.

A sixth preferred mode (x) is the bone morphometric method (i) wherein the image input step is an image reading step in which the quantity of transmitted light determined by irradiating a radiograph including an image of the sample bone and an image of a standard matter having a gradate thickness and formed on an x-ray film, with light and detecting the light transmitted through the radiograph, and the pattern obtaining step includes converting the density pattern into values expressed in terms of the thickness of the standard matter on the basis of the thickness of the standard matter determined from the radiograph formed on the x-ray film and the quantity of transmitted light.

The following are preferred modes of the bone morphometric apparatus (iv) in accordance with the present invention. A first preferred mode (xi) is the bone morphometric apparatus (iv) wherein a boundary point determining means determines the boundary points by determining the first neighborhood point by a predetermined method, determining the internal first regression line in the predetermined range 2 by skipping the predetermined range 1 from the neighborhood point toward the center of the sample bone, determining the outside first regression line in the predetermined range 4 by skipping the range 3 from the neighborhood point away from the center of the sample bone, setting a new neighborhood point at the intersection of the lines, and repeating the foregoing procedure until the new neighborhood point meets a give condition.

A second preferred mode (xii) is the bone morphometric apparatus (iv) wherein a boundary point determining means determines the boundary points by determining the first neighborhood point by a predetermined method, determining the internal first regression line in the predetermined range 2 by skipping the predetermined range 1 from the neighborhood point toward the center of the sample bone, calculating the mean value of the pattern of the quantity of radiations in the predetermined range 4 and determining a straight line of a fixed quantity of radiations passing the mean value by skipping the predetermined range 3 from the neighborhood point away from the center of the sample bone instead of determining the first regression line if the predetermined range 4 does not meet a give condition, setting a new neighborhood point at the intersection of the straight lines, and repeating the foregoing procedure until the new neighborhood point meets a given condition.

A third preferred mode (xiii) is the bone morphometric apparatus (xi) or (xii) wherein a means uses the product of the second difference and the first difference, and/or the second difference to determine the first neighborhood point.

A fourth preferred mode (xiv) is any one of the bone morphometric apparatuses (xi) to (xiii) wherein a means determines a plurality of proposed points by using the product of the second difference and the first difference, and/or the second difference, and selects proposed points meeting a given condition from among the plurality of proposed points in determining the first neighborhood point.

A fifth preferred mode (xv) is the bone morphometric apparatus (xi) wherein the predetermined range 2 is a range between the first neighborhood point and a neighborhood point where the gradient from the first neighborhood point toward the center of the sample bone changes greatly, and the predetermined range 4 is a range between a point where the change of the gradient from the first neighborhood point away from the center of the sample bone meets the given condition 1 and a neighborhood point where the gradient changes greatly.

A sixth preferred mode (xvi) is the bone morphometric apparatus (xv) wherein the given condition (1) is that the product of the first difference and the second difference is smaller than a fixed value.

A seventh preferred mode (xvii) is the bone morphometric apparatus (iv) wherein the process normalizes the values of the pattern of the quantity of transmitted radiations by using the representative of the pattern.

An eighth preferred mode (xviii) is the bone morphometric apparatus (iv) wherein the image input means is an image reading means that detects the quantity of transmitted light determined by irradiating a radiograph including an image of the sample bone and an image of a standard matter and formed on an x-ray film, with light and detecting the light transmitted through the radiograph, and the means for determining the pattern has a conversion means that converts the density pattern into values expressed by the thickness of the standard matter on the basis of the relation between the thickness of the standard matter and the quantity of transmitted light determined from the radiograph formed on the x-ray film.

BRIEF DESCRIPTION OF THE DRAWINGS

The above and other objects, features and advantages of the present invention will be described in detail hereinafter with reference to the accompanying drawings, in which:

FIG. 17 is a graph showing measured data, by way of example, measured by a bone morphometric method in accordance with the present invention;

FIG. 27 is a graph of assistance in explaining a bone axis in a pattern of a bone;

FIGS. 28A through 28C are patterns of the quantity of transmitted radiations measured by a bone morphometric method in accordance with the present invention;

FIGS. 28D and 28E are graphs of assistance in explaining the BMDs of the patterns;

BEST MODE OF CARRYING OUT THE INVENTION

Radiations preferred by the present invention are X-rays and γ-ray. An input image referred to by the present invention is an image formed on an X-ray film by irradiating a sample bone with X-rays or an image formed by irradiating a sample bone with X-rays or gamma rays and detecting the intensity of X-rays or γ-ray transmitted through the sample bone. The present invention uses an ROI (region of interest) determining means for determining an ROI in an input image by a predetermined method.

This predetermined method will be described below.

Figure 1:
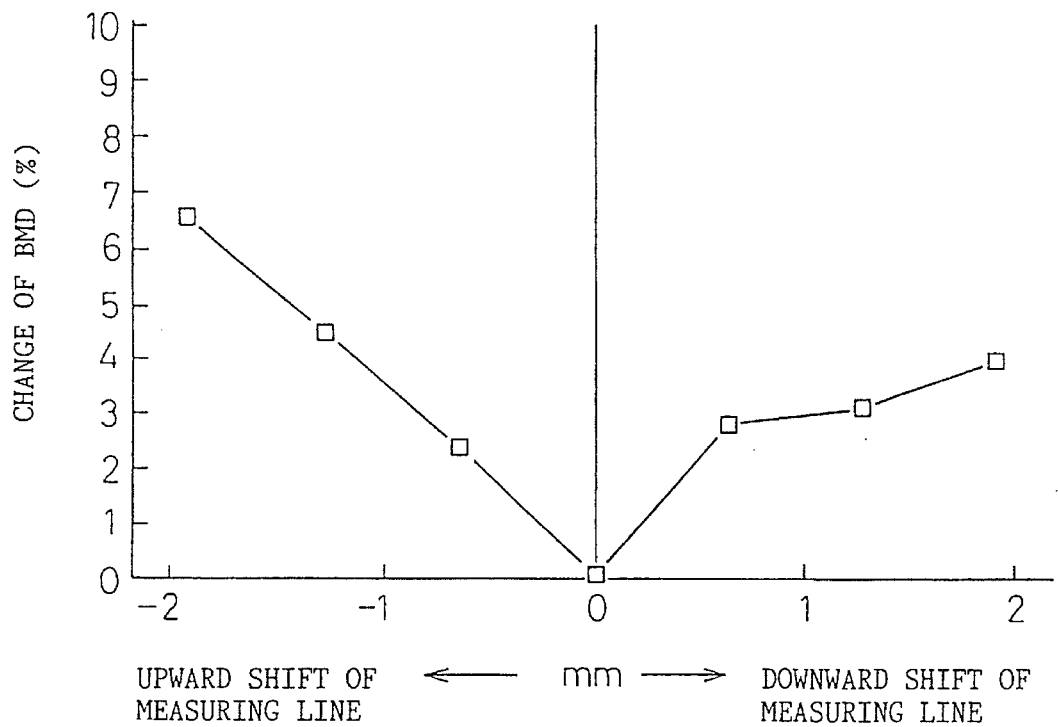
FIG. 1 is a graph showing, by way of example, the dependence of the change of BMD on the shift of measuring line at the distal end of a radius.

The inventors of the present invention found that the shift of a reference measuring line upward or downward relative to a bone axis, i.e., the center line of a bone, is one of the causes that deteriorate the repeatability of measurement. When determining a reference measuring line for the radius by a conventional method, first a reference measuring line is drawn on the basis of the length of the radius and two points are specified on the reference measuring line. When an expert repeats drawing to specify the two points, the accuracy of repeatability is on the order of 0.5 mm at the highest. FIG. 1 shows the dependence of BMD on the dislocation of the reference measuring line from the bone axis. As is obvious from FIG. 1, the BMD changes by about 3% when the reference measuring line is dislocated 1 mm. Thus, the shift of the reference measuring line entails the deterioration of measurement repeatability when the same operator repeats measurement and repeatability varies from operator to operator, which is causes problems in observing the process of changes in the bone of a measurement case.

Figure 2:
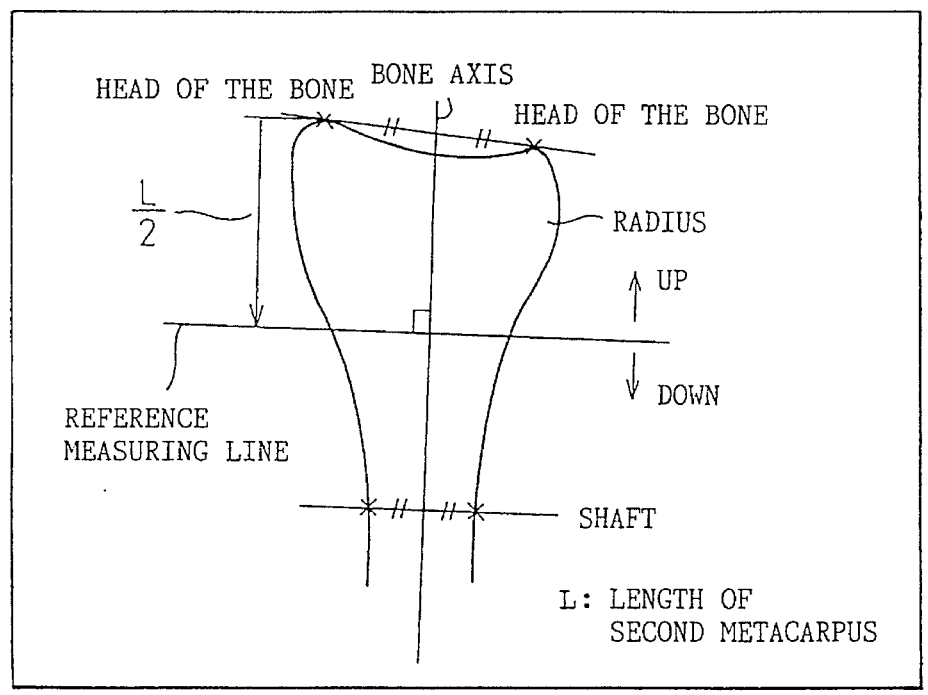
FIG. 2 is graph of assistance in explaining a procedure for specifying reference points in accordance with the present invention.

The inventors of the present invention found that the dislocation of the reference measuring line upward or downward relative to the bone axis can be reduced remarkably by specifying four reference points. As shown in FIG. 2, two points are set at two conspicuous parts in the head of a sample bone, two points are set at two parts on the shaft of the sample bone, a straight line passing the middle points between the two points on the head of the sample bone and the middle point between the two points on the shaft of the sample bone is used as a bone axis, a line perpendicular to the bone axis is drawn automatically at a point on the bone axis at a given distance from the middle point between or one of the two reference points on the head of the sample bone to determine a reference measuring line. The shift of the reference measuring line determined by the method of the present invention is about 50% of that of the reference measuring line determined by the conventional method.

Figure 4:
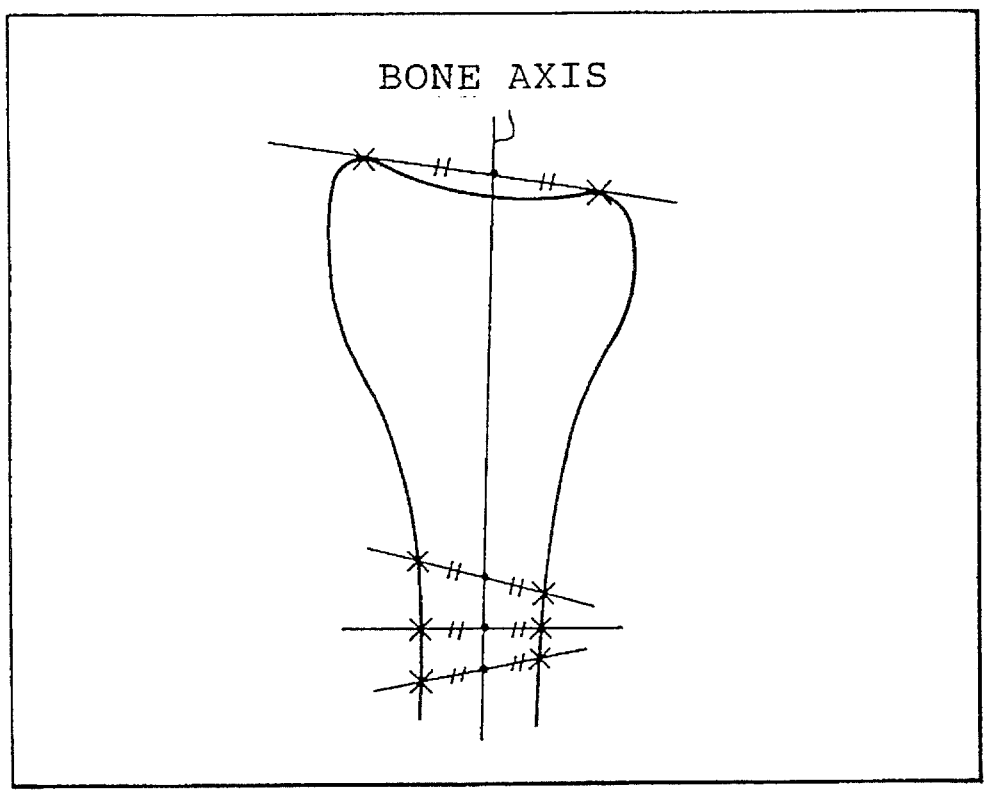
FIG. 4 is a diagrammatic view of assistance in explaining insignificant influence of the dislocation of the reference points on the shaft of a bone on the shift of bone axis.

The effect of mutual compensation of the positional shift of the four reference points on the reduction of overall shift and the effect of automatic drawing on reduction of drawing errors reduce the shift of the reference measuring line. Since most bone-shapes are like a shape shown in FIG. 4, the positions of the two points on the shaft are arbitrary.

TABLE 1

| Variation of position of reference measuring line | Setting method | |
|---|---|---|
| | Conventional | Present Invention |
| Min. | 0.5 mm | 0.00 mm |
| Avg. | 1.0 mm | 0.47 mm |
| Max. | 2.0 mm | 0.80 mm |

Repeatability of reference measuring line setting operation

This improved ROI specifying method not only reduces the upward and downward shift of the reference measuring line, but the same reduces the angular shift () of the reference measuring line attributable to the shift of the bone axis, i.e., a second cause of errors in setting an ROI, and enables the measurement of changes in the BMD with a sufficiently high accuracy.

Figure 3A:
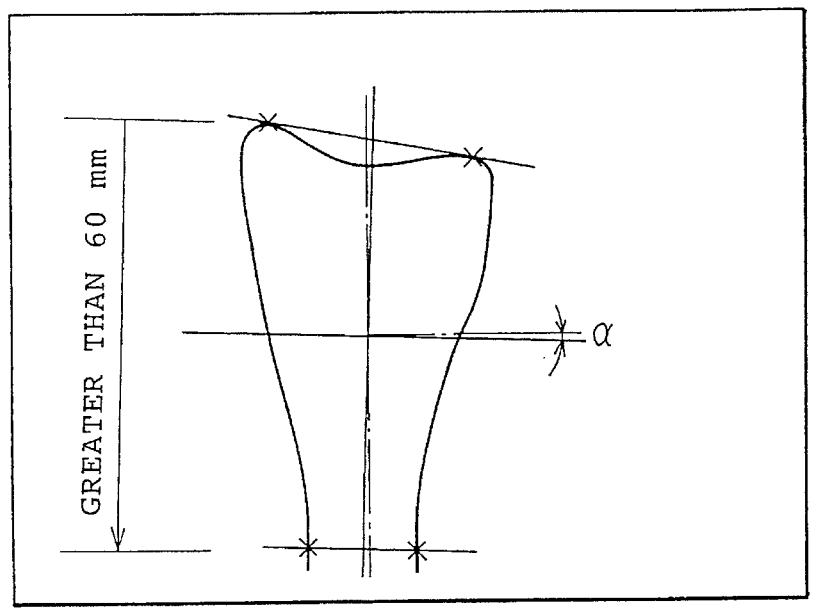
FIG. 3A is a graph of assistance in explaining the insignificant influence of the shift of a bone axis on the change of the angle of a reference measuring line.
Figure 3B:
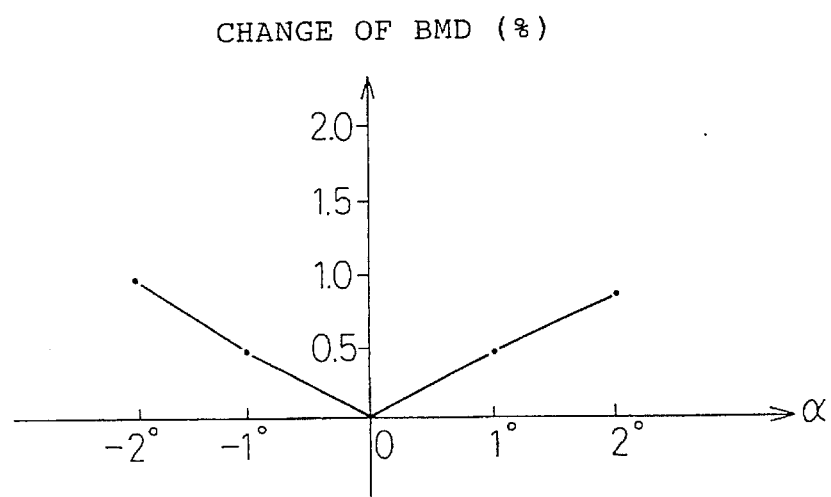
FIG. 3B is a graph of assistance in explaining effective suppression of the change of BMD.

The average distance between the head of the radius of an adult and the reference point on the shaft of the same is 60 mm or above and, empirically, errors in the positions of the reference points are in the range of about 0.3 mm to about 0.5 mm. Therefore, the angular change for maximum angular shift is about 0.7° at the largest as shown in FIG. 3A and the change of the BMD is 0.5% or below as shown in FIG. 3B, when the positional error of the reference point on the head of the radius is 0.5 mm and that of the reference point on the shaft is 0.3 mm.

Figure 5:
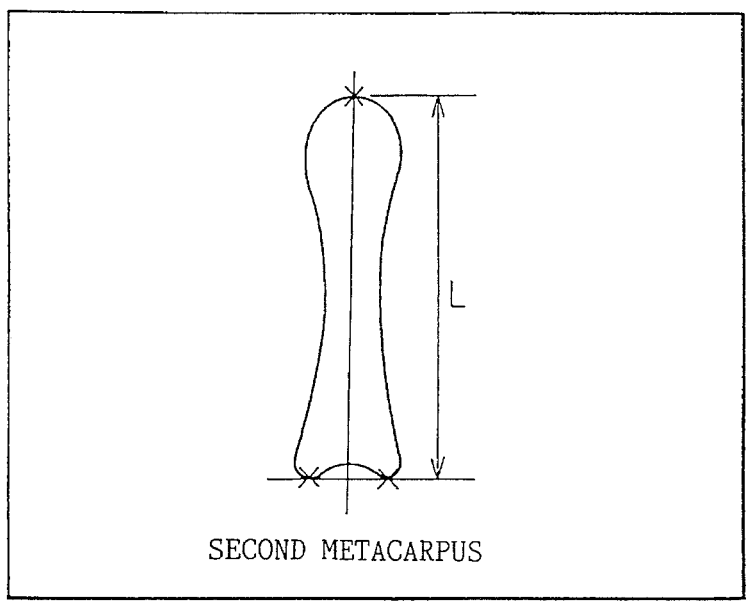
FIG. 5 is a graph of assistance in explaining, by way of example, of a procedure for determining a given distance in accordance with the present invention.
Figure 6:
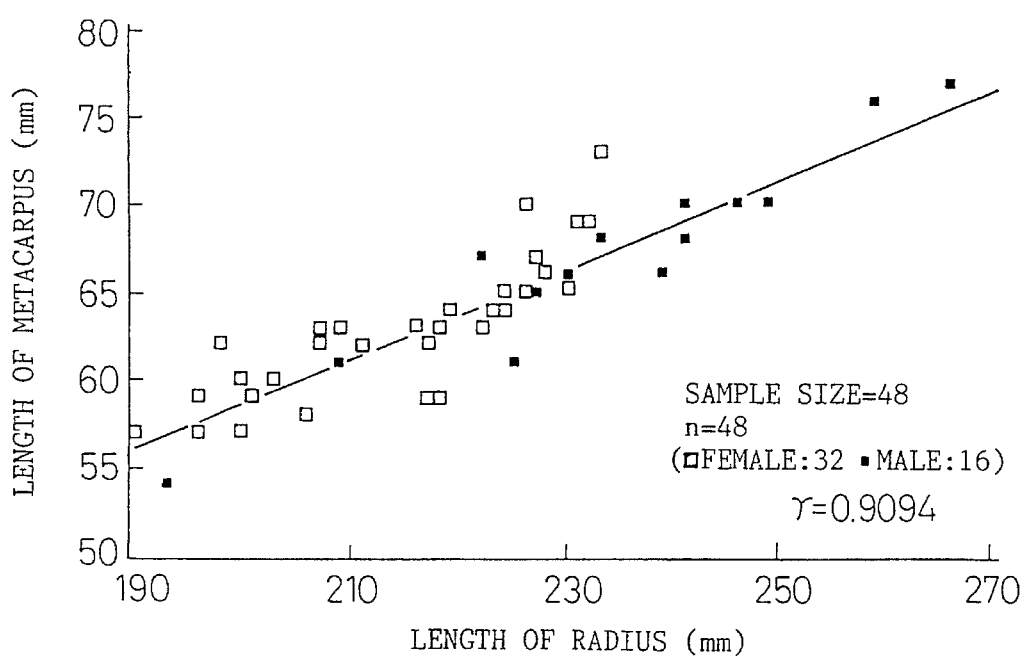
FIG. 6 is a graph showing the relation in length between the metacarpus and the radius.

The length of the metacarpus is used as the given length, and the length of the metacarpus is measured by using three specified points as shown in FIG. 5 to limit errors in drawing and in the measurement of length to very small values. Therefore, the change of the given distance is half the change of the given length determined by using two specified points and the shift of the reference measuring line could be limited to about 25% or below of the shift of the reference measuring line determined by the conventional method. The automatic determination of the reference measuring line enabled quick measurement. Naturally, the distance may be expressed by the length of the radius. However, since both the images of the distal end of the radius and the metacarpus can be formed on x-ray film, and the length of the metacarpus and that of the radius are correlated (coefficient $\gamma$ of correlation $>0.9$) as shown in FIG. 6. For example, the distance of ½ of the length of the metacarpus corresponds to ⅐ of the length of the radius. Accordingly, it is preferable to use the length of the metacarpus as a unit length.

Thus, the reference measuring line is determined, the density of the sample bone is measured along a single measuring line near the sample bone or a plurality of different measuring lines to obtain density patterns of the sample bone, and then the density patterns are processed for measurement by a computer means which measures only a predetermined region of each density pattern.

Means for specifying two points on the head of the sample bone and two points on the shaft of the sample bone in an image of the sample bone may be a CRT, i.e., an image display means, for displaying the image of the sample bone, and a keyboard or a light pen, i.e., a point specifying means for specifying points in the image displayed on the CRT. A means for determining the bone axis by connecting the middle point between the two points on the head of the sample bone and the middle point between the two points on the shaft is, for example, a computer means comprising a ROM storing processing programs, and a RAM for arithmetic operation and temporary data storage.

A system including a reference measuring line setting means for setting a reference measuring line perpendicularly intersecting the bone axis at a point at a given distance from one of, or the middle point between, the two points on the head of the sample bone, a pattern forming means for forming a pattern of the quantity of transmitted radiations transmitted through the sample bone along the reference measuring line, or a single or a plurality of measuring lines near the reference measuring line, and a measuring means for processing the patterns by predetermined arithmetic operations for the measurement of the sample bone is, for example, a computer means comprising a ROM storing the contents of the process, a RAM for arithmetic operation and temporary data storage, and a CPU.

In a pattern of the quantity of transmitted light determined by irradiating an x-ray film, having both an image of the sample bone and that of a standard matter, with light and detecting transmitted light, the density of the image of the sample bone can be converted into density data expressed in terms of the thickness of the standard matter by comparing the quantity of transmitted light transmitted through the image of the sample bone with the quantity of transmitted light transmitted through the image of the standard matter, which reduces errors attributable to the variation of the density of the images formed on the x-ray film dependent on x-raying conditions. The standard matter is a wedge-shaped standard block having continuously gradate thickness or a stepped standard block having thickness varying in steps of 1 mm. When the wedge-shaped standard block is used, the quantity of transmitted light transmitted through the image of the sample bone is compared directly with that of transmitted light transmitted through the image of the wedge-shaped standard block to convert the quantity of transmitted light into data expressed in terms of the thickness of the wedge-shaped standard block. When converting the quantity of transmitted light transmitted through the image of the sample bone into data expressed in terms of the respective thicknesses of steps of the stepped standard block and the quantity of transmitted light transmitted through the image of the sample bone corresponds to a thickness between those of the adjacent steps of the stepped standard block, a thickness corresponding to the quantity of transmitted light transmitted through the image of the sample bone is determined by linear interpolation or spline interpolation. These arithmetic operations are performed by the aforesaid computer means comprising the ROM, the RAM and the CPU.

Figure 7:
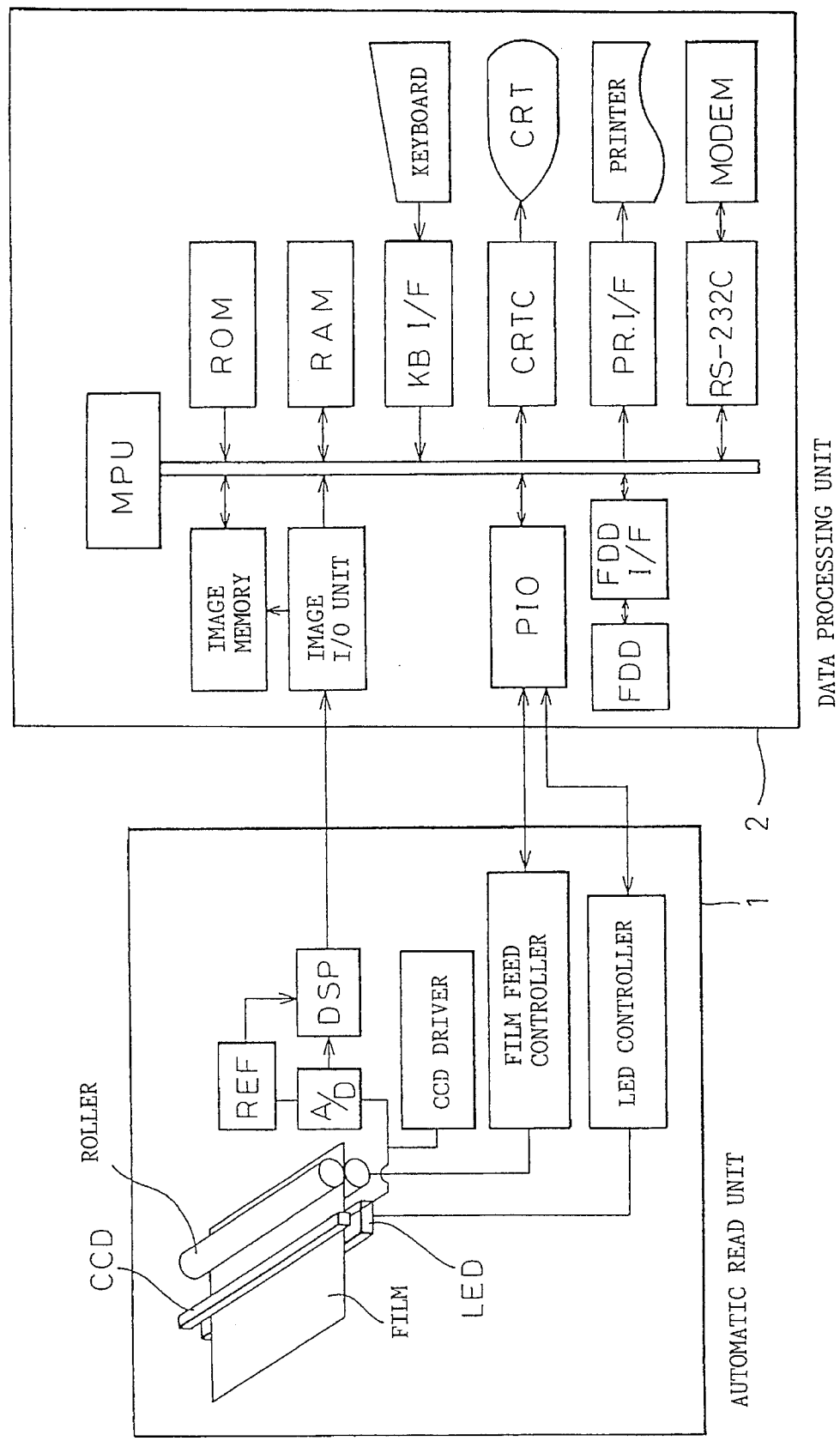
FIG. 7 is a block diagram of a bone morphometric apparatus in a preferred embodiment according to the present invention.

Referring to FIG. 7 showing a bone morphometric apparatus in a preferred embodiment according to the present invention, an automatic read unit 1 comprises a linear image sensor (CCD) for detecting signals, i.e., the intensity of light transmitted through a radiograph formed on an x-ray film and corresponding to the density of the radiograph formed on the x-ray film, extended perpendicularly to a film feed direction, a linear light source (LED) for irradiating the x-ray film with light from above or from below the same, a rod lens for focusing transmitted light transmitted through the radiograph formed on the x-ray film on the linear sensor, and a film moving device for moving the x-ray film minutely with a stepping motor.

A film feed controller, i.e., a control means, controls the movement of the x-ray film to detect transmitted light transmitted through only a specified region on the x-ray film and makes the x-ray film move intermittently at a given speed. A CCD driver has a control function to read data stored in the CCD at predetermined time. A LED controller is a luminous intensity adjusting means for adjusting the luminous intensity of the light emitted by a light source according to the level of density of the radiograph formed on the x-ray film.

Figure 8:
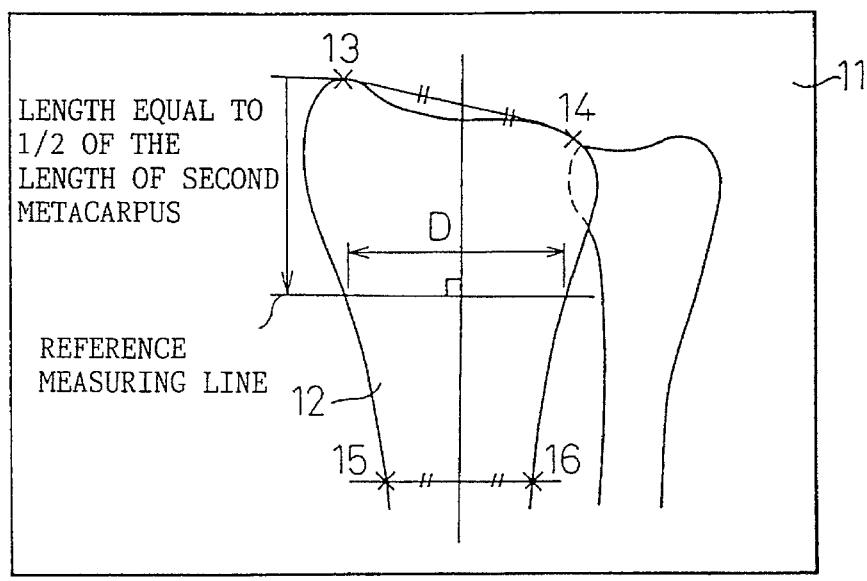
FIG. 8 is a graph of assistance in explaining a procedure for setting a measuring line by a bone morphometric method in accordance with the present invention.

FIG. 8 illustrates an enlarged image of the radius displayed on the CRT, i.e., an image display means, included in a data processing unit 2 shown in FIG. 7. Shown in FIG. 8 are a screen 11, an image 12 of the radius, reference points (picked points) 13, 14, 15 and 16 necessary for bone measurement. More concretely, it is preferable for ensuring satisfactory positional repeatability to use a reference measuring line determined by connecting the middle point between the reference points 13 and 14 and the middle point between the reference points 15 and 16, and drawing a line perpendicular to the line connecting the middle points at a point at a given distance, such as a distance equal to ½ of the length of the second metacarpus. The reference points may be specified by a cursor moving means, a light pen input means or a touch panel input means.

Data read by the automatic read unit 1 of FIG. 7 is stored in an image storage device comprising, as principal components, an image I/O unit of the data processing unit, and an image memory. The stored image data is displayed in an enlarged pattern of the sample bone as shown in FIG. 9 by an image display device comprising, as principal components, a CRTC and a CRT.

An arithmetic means included in the bone morphometric apparatus of the present invention may be of any type, provided that the arithmetic means is capable of determining a predetermined measuring region in the image of the sample bone stored in the image storage device with reference to the reference points specified by the point specifying means, of converting the image data of the predetermined region in the image of the sample bone into data expressed by the thickness of the standard matter by using the stored data on the respective images of the sample bone and the standard matter and of processing the data for bone measurement. A microcomputer means comprising a ROM storing arithmetic programs for bone measurement, and a RAM for arithmetic operation and temporary data storage is an example of the arithmetic means.

Figure 9:
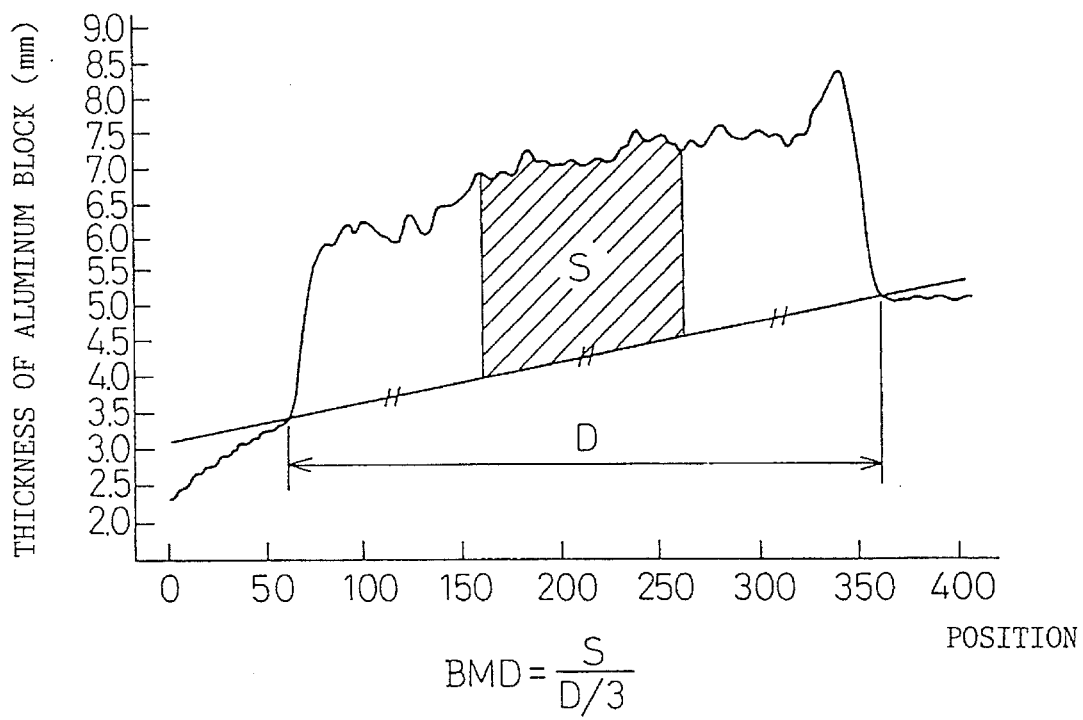
FIG. 9 is a graph showing measured data measured by the present invention.

FIG. 9 illustrates a pattern representing the stored image data acquired along the given measuring line at the distal end of the radius and expressed in terms of the thickness of the standard matter, in which a bone density distribution in a region along the bone width D is shown.

An RS232C port and a MODEM in FIG. 7 are communication means for communication between the bone morphometric apparatus and a bone assaying system, and a PIO port is an interface through which digital control inputs are given to a computer system.

Although this embodiment employs x-ray film, the present invention is readily applicable to an apparatus that forms an image of a sample bone on an x-ray image sensor by irradiating the sample bone with X-rays.

Figure 10:
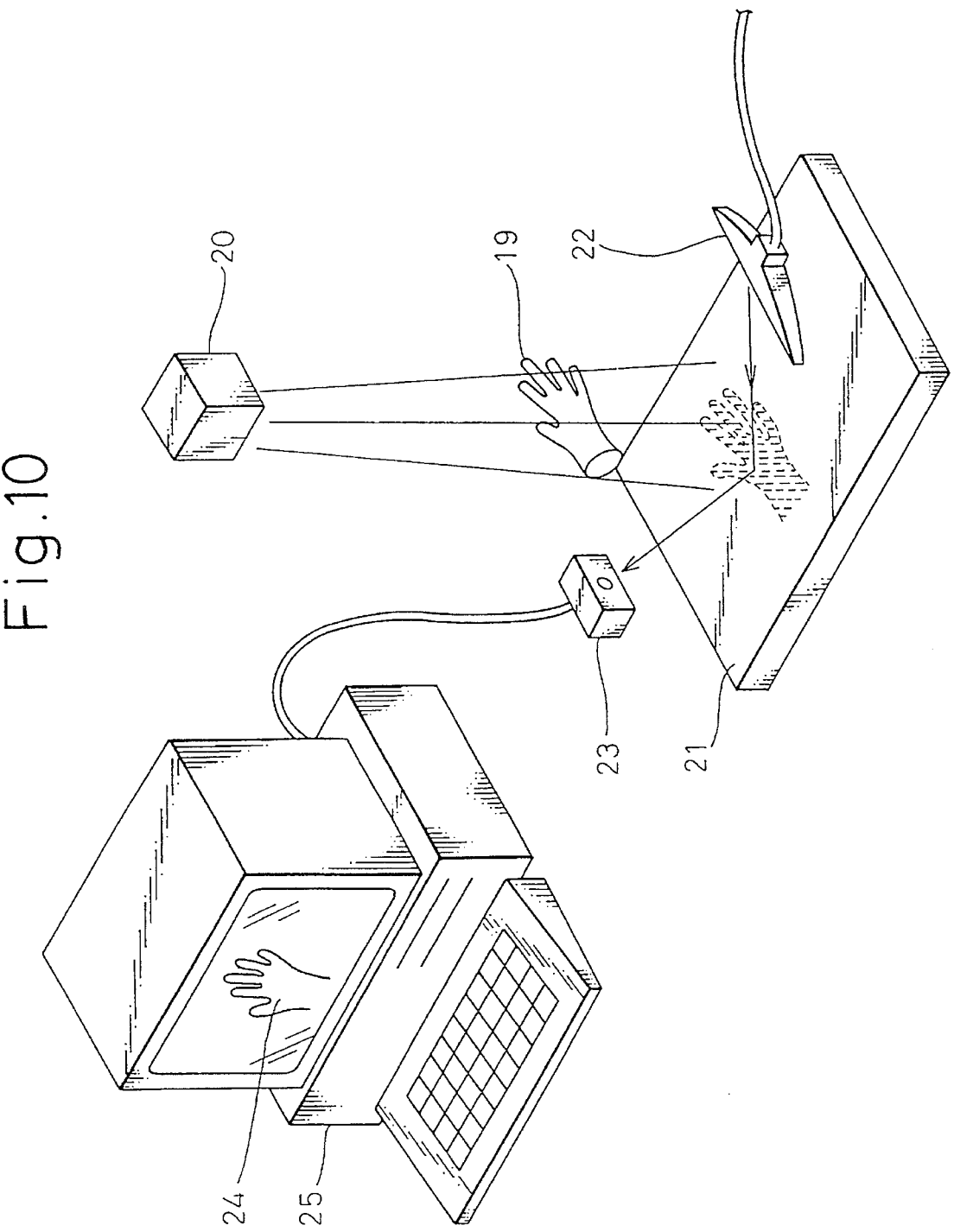
FIG. 10 is a perspective view of an image forming system for forming an image of a sample bone by irradiating the sample bone on an x-ray image sensor with X-rays in carrying out the present invention.

FIG. 10 systematically illustrates the construction and arrangement of the bone morphometric apparatus according to the present invention, for carrying out a series of operations from an x-raying operation for forming an x-ray image of a sample bone to a bone morphometric operation.

An image forming apparatus that irradiates an x-ray image sensor directly together with a sample bone 19 with X-rays emitted by an x-ray source 20 uses an imaging plate 21 instead of a film cassette containing an x-ray film, which is employed in the conventional roentgenography. X-ray information recorded on the imaging plate 21 is read by irradiating the x-ray information with a laser beam emitted by a laser light emitting means 22 and by detecting the laser beam by an optical detector 23 to obtain light signals representing the intensities of X-rays. An image processing unit 25 subjects photoelectric information read from the imaging plate to A/D conversion to obtain an x-ray image of the sample bone, and the x-ray image is processed for bone measurement in accordance with the present invention.

The present invention includes a bone morphometric apparatus that uses an image represented by the quantity of transmitted gamma rays, obtained by irradiating a sample bone with gamma rays and detecting transmitted gamma rays by photon absorptiometry.

The bone morphometric method and the bone morphometric apparatus described above reduce personal errors and repetition errors, and achieve accurate bone measurement.

A second embodiment according to the present invention will be described hereinafter.

The second embodiment, similarly to the first embodiment, determines an ROI (region of interest) in an input image by a predetermined method, forms patterns of the radiation transmitted through a sample bone along a single or a plurality of measuring lines near the image of the sample bone, and processes only a predetermined region in each pattern for bone measurement by a computer means.

The predetermined method specifies two points at conspicuous positions on the head of the sample bone, determines the middle point between the two points on the head of the sample bone, specifies two points on the shaft of the sample bone, determines the middle point between the two points on the shaft, interconnects the middle points by a line to use the same line as a bone axis, draws a line perpendicularly to the bone axis at a position at a given distance from the middle point between or one of the two points on the head of the sample bone, and draws a plurality of parallel lines at equal intervals near the line perpendicular to the bone axis to use the plurality of measuring lines as ROIs.

The computer means comprises a MPU that executes instructions, a ROM for storing bone measuring programs and instructions, and a RAM for arithmetic operation and temporary data storage.

Figure 11:
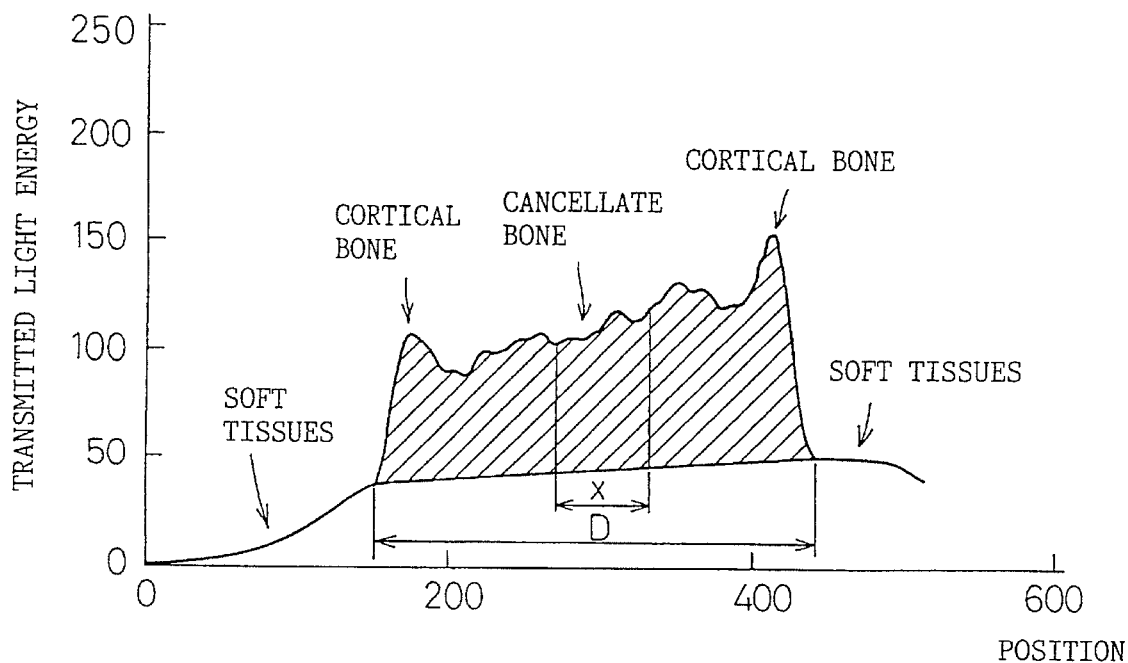
FIG. 11 is a graph showing measured data measured by the conventional bone morphometric apparatus.

A procedure for determining a predetermined region will be described hereinafter. As mentioned above, bones are classified into cortical bones and cancellate bones. Since the conventional bone morphometric method calculates bone density for the pattern of the quantity of transmitted radiations along the entire bone width D (FIG. 11) and it is impossible to measure the cortical bone and the cancellate bone separately.

Figure 12:
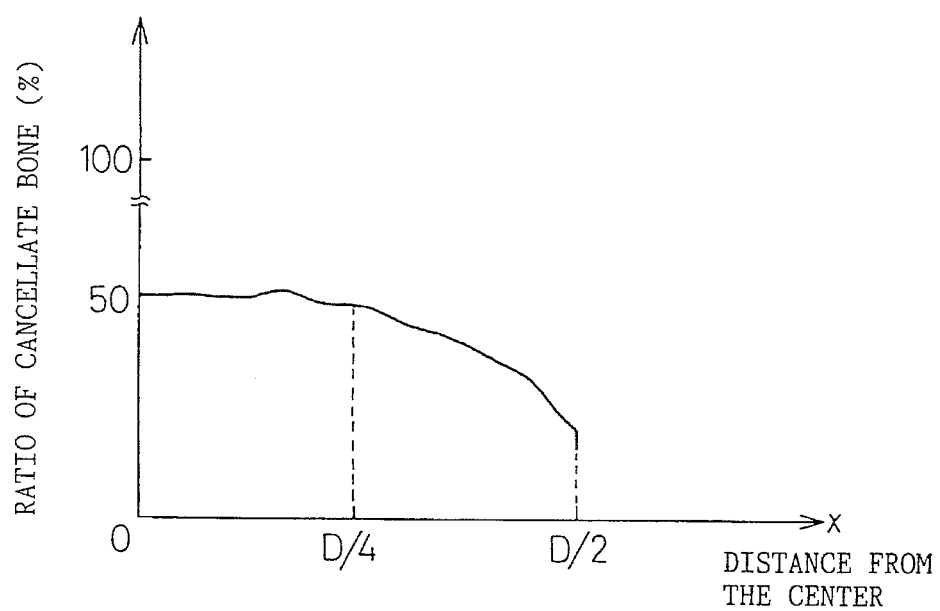
FIG. 12 is a graph showing the ratio of a cancellate bone.
Figure 13:
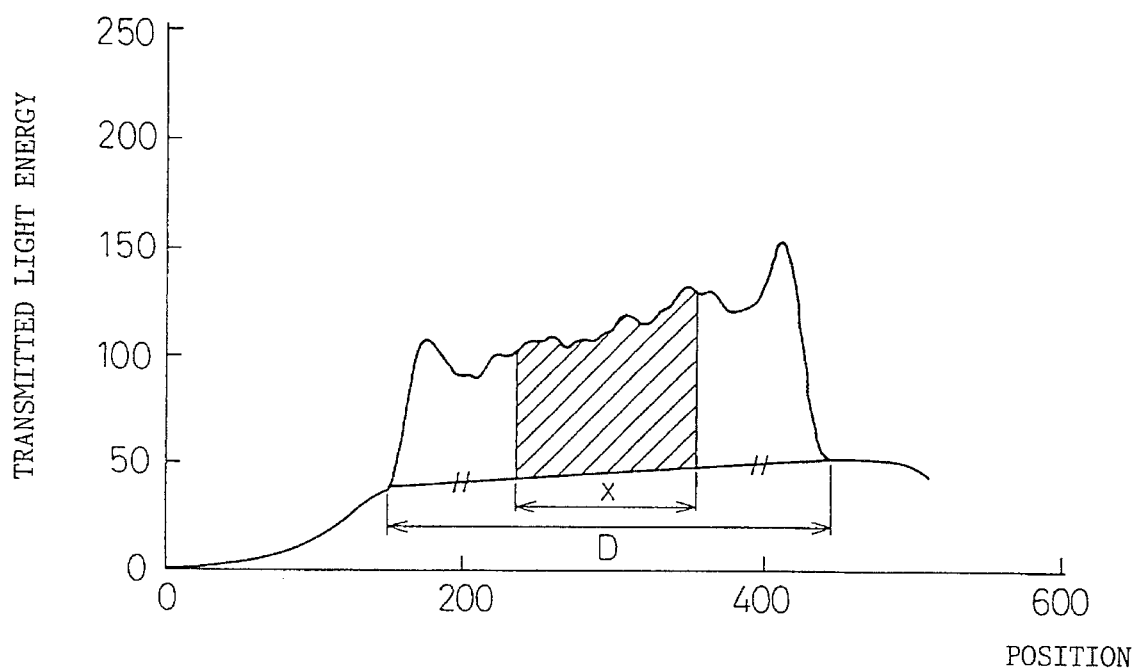
FIG. 13 is a graph showing measured data on a cancellate bone.

According to the present invention, the bone density of only a portion of the sample bone in a predetermined region x (FIG. 11) of the pattern of the quantity of transmitted radiations is calculated. As shown in FIG. 12 typically illustrating the variation in half of the bone width, the ratios of cortical bone and cancellate bone vary with the distance from the bone axis. Therefore, the width of the region must be narrow to measure only either cortical bone or cancellate bone. For example, when it is desired to measure a region mostly including cancellate bone, the data on a shaded region of a pattern shown in FIG. 13 is processed.

However, if a narrow region is specified, the variation of the data increases due to the positional variation of the properties of the bone and the dislocation of the measuring line attributable to the dispersion of the sensitivity of the measuring system and, consequently, the measuring accuracy (Coefficient of Variance: CV) drops as shown in FIG. 14.

Figure 14:
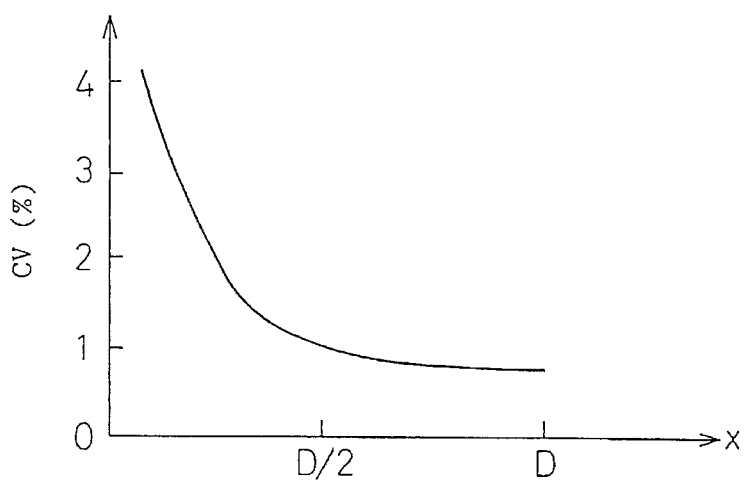
FIG. 14 is a graph showing the dependence of measuring accuracy on measuring region.

As shown in FIGS. 12 and 14, the ratio of cancellate bone and the measuring accuracy CV are dependent on each other; that is, when a required ratio of bone is determined, the accuracy is fixed accordingly, or when the accuracy is specified, the ratio of bone is fixed accordingly. The present invention enables the measurement of a region mostly including cancellate bone with a high accuracy through the rational determination of a region for measurement. It is preferable to specify the width of a region by a value expressed by the bone width D as shown in FIG. 15.

Figure 15:
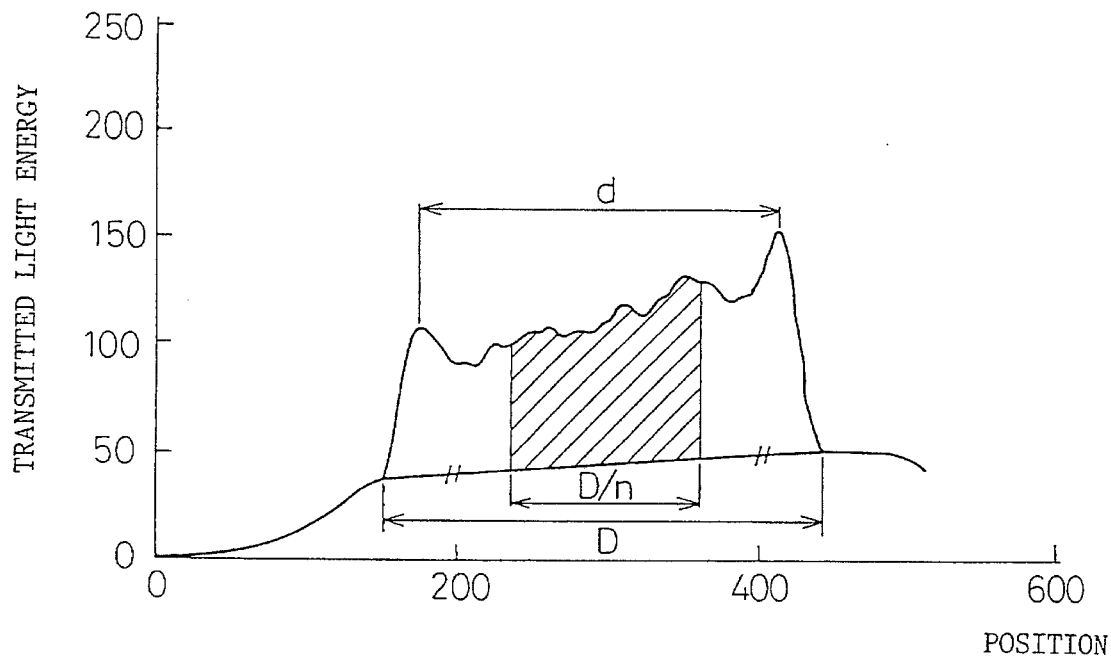
FIG. 15 is a graph showing measured data measured by a bone morphometric method in accordance with the present invention.
Figure 16:
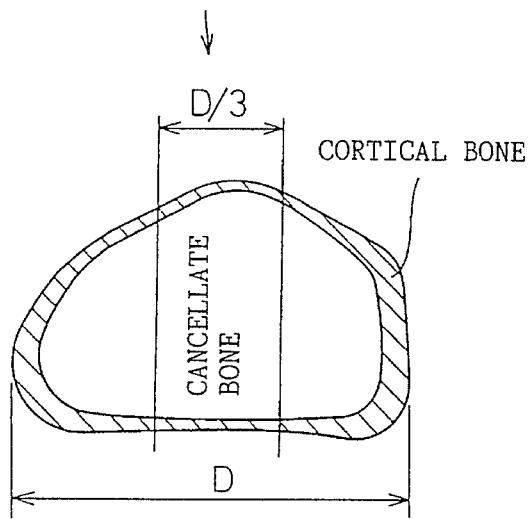
FIG. 16 is a typical view showing a measuring point at the distal end of the radius.

Referring to FIG. 15, use of a peak-to-peak distance d for the measurement of cortical bone for the region mostly including cancellate bone is not desirable because, in most cases, the peak-to-peak distance d is indefinite in a region mostly including cancellate bone. Bone distribution in a region of a width equal to ⅛ of the length of the radius is similar to that shown in FIG. 16. When the measurement of cancellate bone is desired, a region in which the ratio of cancellate bone is 50% can be measured at a CV of 2% or below as shown in FIGS. 12 and 14, when the width of the region is ⅓ of the bone width D.

The bone morphometric apparatus in the second embodiment according to the present invention is identical to the bone morphometric apparatus shown in FIG. 7. An automatic read unit 1 comprises a linear image sensor (CCD) for detecting signals, i.e., the intensity of light transmitted through a radiograph formed on an X-ray film and corresponding to the density of the radiograph formed on the X-ray film, extended perpendicularly to a film feed direction, a linear light source (LED) for irradiating the X-ray film with light from above or from below the same, a rod lens for focusing transmitted light transmitted through the radiograph formed on the X-ray film on the linear sensor, and a film moving device for moving the X-ray film minutely with a stepping motor.

A film feed controller, i.e., a control means, controls the movement of the X-ray film to detect transmitted light transmitted through only a specified region on the X-ray film and makes the X-ray film move intermittently at a given speed. A CCD driver has a control function to read data stored in the CCD at predetermined time. An LED controller is a luminous intensity adjusting means for adjusting the luminous intensity of light emitted by a light source according to the level of density of the radiograph formed on the X-ray film.

Means for specifying two points on the head of the sample bone and two points on the shaft of the sample bone in an image of the sample bone may be a CRT, i.e., an image display means, for displaying the image of the sample bone, and a keyboard or a light pen, a point specifying means for specifying points in the image displayed on the CRT. A means for determining the bone axis by connecting the middle point between the two points on the head of the sample bone and the middle point between the two points on the shaft is, for example, a computer means comprising a ROM for storing processing programs, and a RAM for arithmetic operation and temporary data storage.

A system including a reference measuring line setting means for setting a reference measuring line perpendicularly intersecting the bone axis at a point at a given distance from one of or the middle point between the two points on the head of the sample bone, a pattern forming means for forming patterns of the quantity of transmitted radiations transmitted through the sample bone along the reference measuring line, or a single or a plurality of measuring lines near the reference measuring line, and a measuring means for processing the patterns by predetermined arithmetic operations for the measurement of the sample bone is, for example, a computer means comprising a ROM for storing a contents of the process, a RAM for arithmetic operation and temporary data storage, and a CPU.

In a pattern of the quantity of transmitted light determined by irradiating an x-ray film having both an image of the sample bone and that of a standard matter with light and detecting transmitted light, the density of the image of the sample bone can be converted into density data expressed in terms of the thickness of a standard matter by comparing the quantity of transmitted light transmitted through the image of the sample bone with the quantity of transmitted light transmitted through the image of the standard matter, which reduces errors attributable to the variation of the density of the images formed on the x-ray film dependent on the x-raying conditions. The standard matter is a wedge-shaped standard block having continuously gradate thickness or a stepped standard block having thickness varying in steps of 1 mm. When the wedge-shaped standard block is used, the quantity of transmitted light transmitted through the image of the sample bone is compared directly with that of transmitted light transmitted through the image of the wedge-shaped standard block to convert the quantity of transmitted light into data expressed by the thickness of the wedge-shaped standard block. When converting the quantity of transmitted light transmitted through the image of the sample bone into data expressed by the respective thicknesses of steps of the stepped standard block and the quantity of transmitted light transmitted through the image of the sample bone corresponding to a thickness between those of the adjacent steps of the stepped standard block, a thickness corresponding to the quantity of transmitted light transmitted through the image of the sample bone is determined by linear interpolation or spline interpolation. These arithmetic operations are performed by the aforesaid computer means comprising the ROM, the RAM and the CPU.

The bone morphometric apparatus of FIG. 7 displays an enlarged image of the radius on the CRT, i.e., an image display means, as shown in FIG. 8.

Figure 18B:
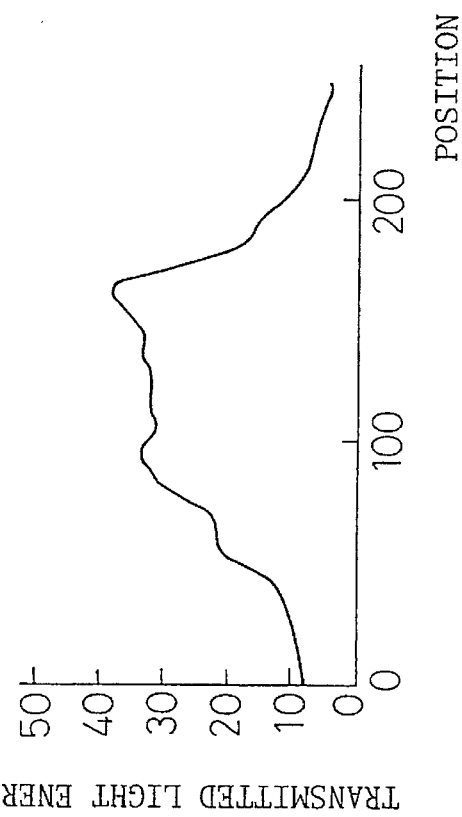
FIG. 18B is a graph of assistance in explaining in appropriate pattern composition.
Figure 18A:
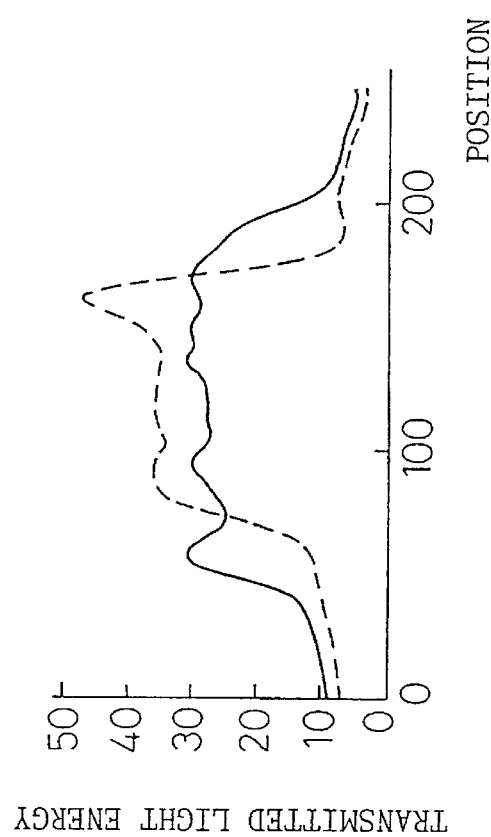
FIG. 18A is a graph showing a plurality of patterns before composition.

Image data read by the bone morphometric apparatus of FIG. 7 is stored by an image storage means comprising, as principal components, the image I/O unit of a data processing unit, and an image memory. The stored image data is displayed as an enlarged pattern of the sample bone as shown in FIG. 18 by an image display means comprising, as principal components, the CRT and a CRTC.

An arithmetic means included in the bone morphometric apparatus of the present invention may be of any type, provided that the arithmetic means is capable of determining a predetermined measuring region in the image of the sample bone stored in the image storage means with reference to the reference points specified by the point specifying means, such as a cursor key, of converting the image data of the predetermined region in the image of the sample bone into data expressed in the terms of the thickness of the standard matter by using the stored data on the respective images of the sample bone and the standard matter and of processing the data for bone measurement. A microcomputer means comprising a ROM for storing arithmetic programs for bone measurement, and a RAM for arithmetic operation and temporary data storage is an example of the arithmetic means.

A computer means comprising a ROM for storing arithmetic programs and a RAM for arithmetic operation and temporary data storage is an example of a system comprising a means for measuring patterns of the quantity of transmitted radiations transmitted through the sample bone along a single or a plurality of measuring lines in a measuring region in the image of the sample bone, and a means for measuring the sample bone by processing the pattern only in a predetermined local region determined on the basis of the bone width of the sample bone.

FIG. 17 illustrates a pattern of the stored image data along the predetermined measuring line in the distal end of the radius expressed by the thickness of the standard matter, in which a bone density distribution in a region of a width equal to ⅓ of the bone width D is shown.

In the second embodiment also, the RS232port and MODEM of FIG. 7 are communication means for communication between the bone morphometric apparatus and a bone assay system, and PIO is an interface through which digital control inputs are given to a computer system.

Although the above-mentioned example employs the x-ray film, the present invention is readily applicable to an apparatus that forms an image of a sample bone on an x-ray image sensor by irradiating the sample bone with X-rays.

A system of this bone morphometric apparatus for carrying out a series of operations from an operation for forming an X-ray image of the sample bone to a bone measuring operation, similarly to the aforesaid system, has a configuration as shown in FIG. 10.

Referring to FIG. 10, an image forming apparatus that directly irradiates an X-ray image sensor with X-rays from X-ray source 20 together with a sample bone 19 uses an imaging plate 21 instead of a film cassette containing an x-ray film, which is employed in the conventional roentgenography. X-ray information recorded on the imaging plate 21 is read by irradiating the X-ray information with a laser beam emitted by a laser light emitting means 22 and by detecting the laser beam by an optical detector 23 to obtain light signals representing the intensities of x-rays. An image processing unit 25 subjects photoelectric information read from the imaging plate to A/D conversion to obtain an x-ray image of the sample bone, and the x-ray image is processed for bone measurement in accordance with the present invention.

The present invention includes a bone morphometric apparatus that uses an image represented by the quantity of transmitted gamma rays, obtained by irradiating a sample bone with gamma rays and detecting transmitted gamma rays by photon absorptiometry.

Another embodiment of the present invention provides the bone morphometric method and the bone morphometric apparatus capable of accurately and rationally measuring the BMDs of cortical bones and cancellate bones.

A still further embodiment of the present invention will be described hereinafter.

Since a practical pattern in which a region of interest (ROI) by a predetermined method includes noise, the noise must be eliminated when processing a pattern by the second embodiment. Smoothing patterns of the quantity of transmitted radiations in a narrow area in the entire measuring area, i.e., the composition of patterns, is a simple measure to eliminate the noise and to produce a satisfactory result. However, the more the number of patterns are composed, and the higher is the effect of noise elimination, the patterns of a cancellate bone, such as the radius, are distorted as mentioned with reference to FIGS. 18A and 18B. Empirically, it is preferable to use five measuring lines or so (approximately 0.3 mm) for the distal end of the radius when an image formed on an x-ray film is scanned with a sensor having a resolution on the order of 63.5 μm.

Figure 19A:
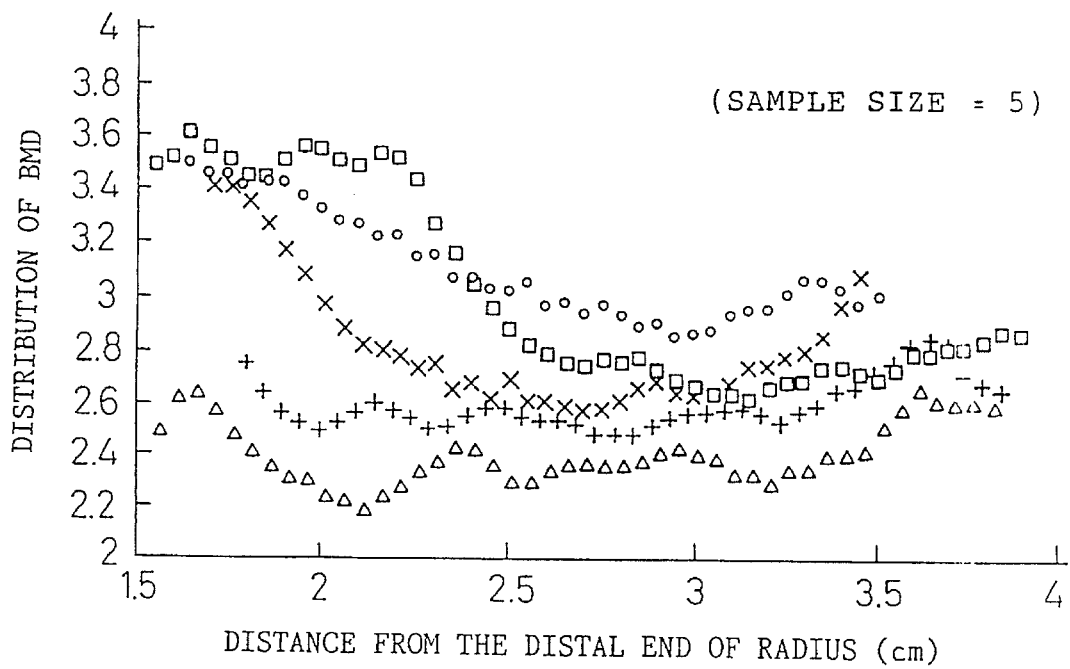
FIG. 19A is a graph showing the relation between BMD and measuring points on the radius.

As shown in FIG. 19A, the BMD varies in a wide range when the measuring line (FIG. 19B) of a pattern shifts. The BMD can be accurately and stably measured with satisfactory repeatability by determining BMDs in narrow areas along a plurality of measuring lines, and averaging the BMDs in a wider area.

The size of the wider area is dependent on the stability of the data on the measuring part and required measuring accuracy.

Figure 19B:
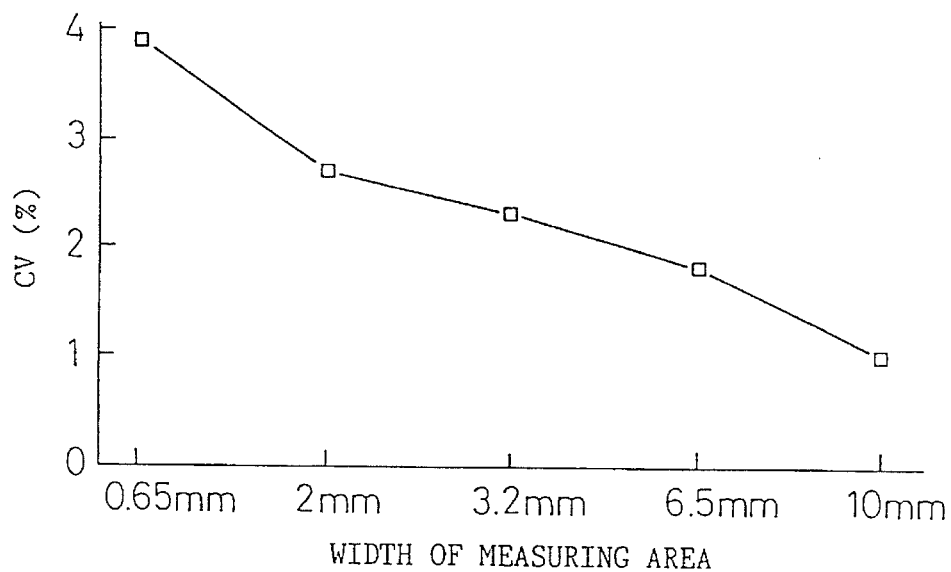
FIG. 19B is a graph showing the dependence of accuracy on measuring width in measuring a cancellate bone.
Figure 20:
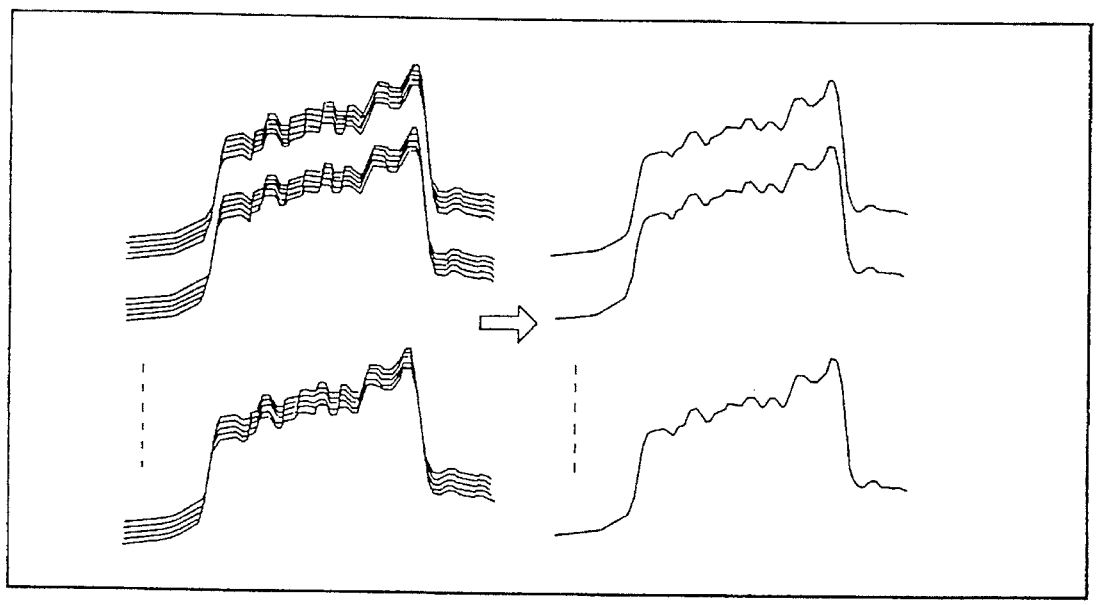
FIG. 20 is a graph of assistance in explaining a smoothing procedure in carrying out a bone measuring method in accordance with the present invention.

FIG. 19B illustrates the relationship between a measuring area around a position at a distance equal to ½ of the length of the second metacarpus from the distal end of the radius, and CV. From FIG. 19B, the size of the measuring area (width) necessary for improving the accuracy by 1% is 10 mm.

If an excessively large amount of data needs to be processed to process density patterns corresponding to all the measuring lines in the measuring area, an excessively long time is required for calculation, which is practically infeasible. Therefore, narrow areas separated at intervals are used instead of successive narrow patterns when obtaining a composite pattern to solve the foregoing problem.

It was found that, when five patterns corresponding to five measuring lines included in a narrow area of 317.5 μm among parallel patterns of the quantity of transmitted radiations arranged at intervals of 63.5 μm in a measuring area are composed in a single pattern, the BMD changes scarcely when every other BMD determined from the composite patterns is selected and the selected BMDs are averaged, but that the BMD changes when more BMDs are omitted. Therefore, it is preferable to average the BMDs of the patterns remaining after omitting the BMD of every other composite pattern composed by five patterns corresponding to five measuring lines. If the composed pattern (smoothed pattern) cannot be satisfactorily recognized and abnormal parameters are obtained, the abnormal parameters must be rejected and removed from the data to be processed for the averaging to remain accurate. When necessary, low-level noise may be eliminated by calculating a running mean before determining the BMD from the composite pattern.

A method of rejecting abnormal parameters will be described in detail. Generally, the physical properties of a bone change continuously to form a structure in which stress concentration does not occur. Therefore, it is possible to find measured abnormal parameters by finding a position where the bone width and the BMD changes sharply.

Figure 21:
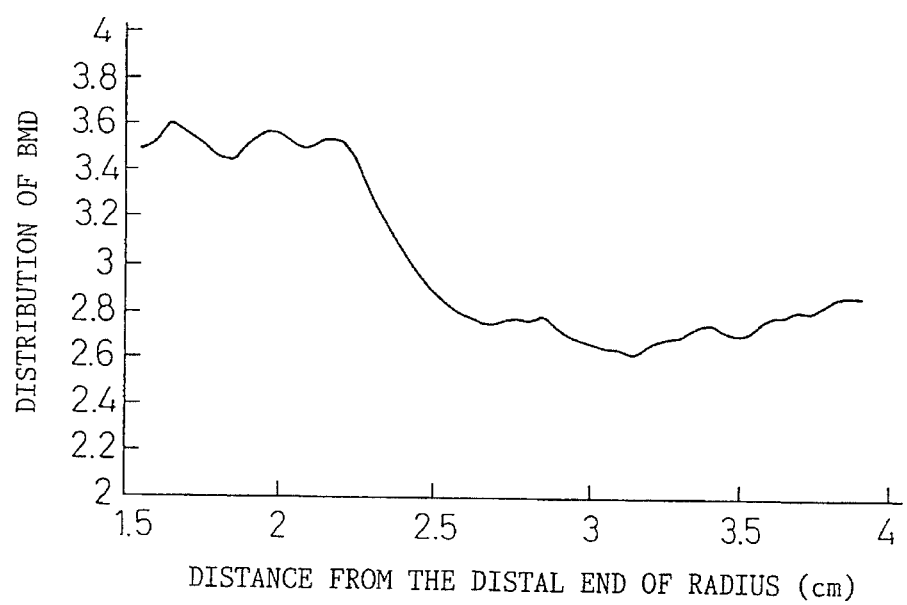
FIG. 21 is a graph showing the relation between the distribution of BMD and measuring part when a smoothing process is used in carrying out a bone morphometric method in accordance with the present invention.
Figure 22:
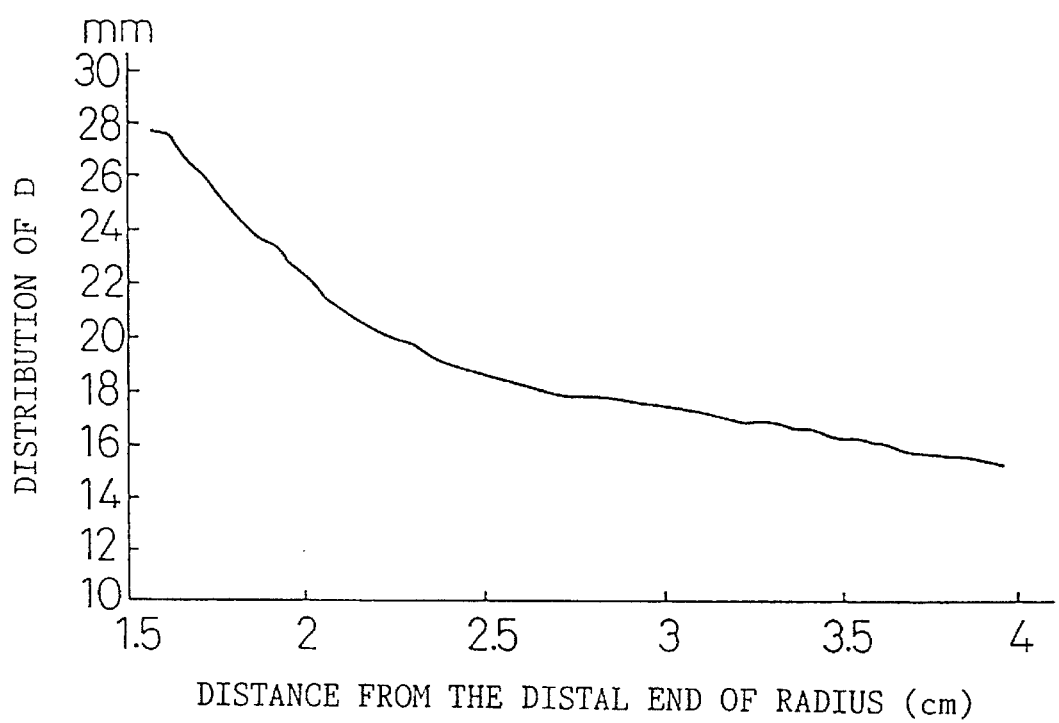
FIG. 22 is a graph showing the relation between measuring part and bone width when a smoothing process is used in carrying out a bone morphometric method in accordance with the present invention.

FIG. 21 illustrates the variation of BMD and FIG. 22 illustrates the variation of bone width D. BMD changes greatly at a position where the ratio of the cancellate bone start increasing. Therefore, it is difficult to decide whether the change of BMD is due to abnormal parameters or whether the same is due to the change of the properties of the bone by the method of finding abnormal parameters from the change of BMD. The method that finds abnormal parameter on the basis of bone width D is preferable because bone width does not change sharply and abnormal parameters can be easily found. A measured bone width is compared with a bone width determined on the basis of the next pattern, and the difference between the bone widths is examined to see of the difference is greater than an allowable value to maintain the accuracy of parameters. Preferably, the allowable value is determined by measuring images formed on a plurality of x-ray films, calculating the standard deviation of the differences between the adjacent widths, and a suitable allowable value is 3σ. It is preferable to use the bone width of a portion of a bone in which stable data can be obtained as a reference bone width.

It is preferable to use the width of, for example, the central portion or the lower portion (portion having a readily recognizable pattern) of a region at the distal end of the radius as the reference bone width.

Figure 23:
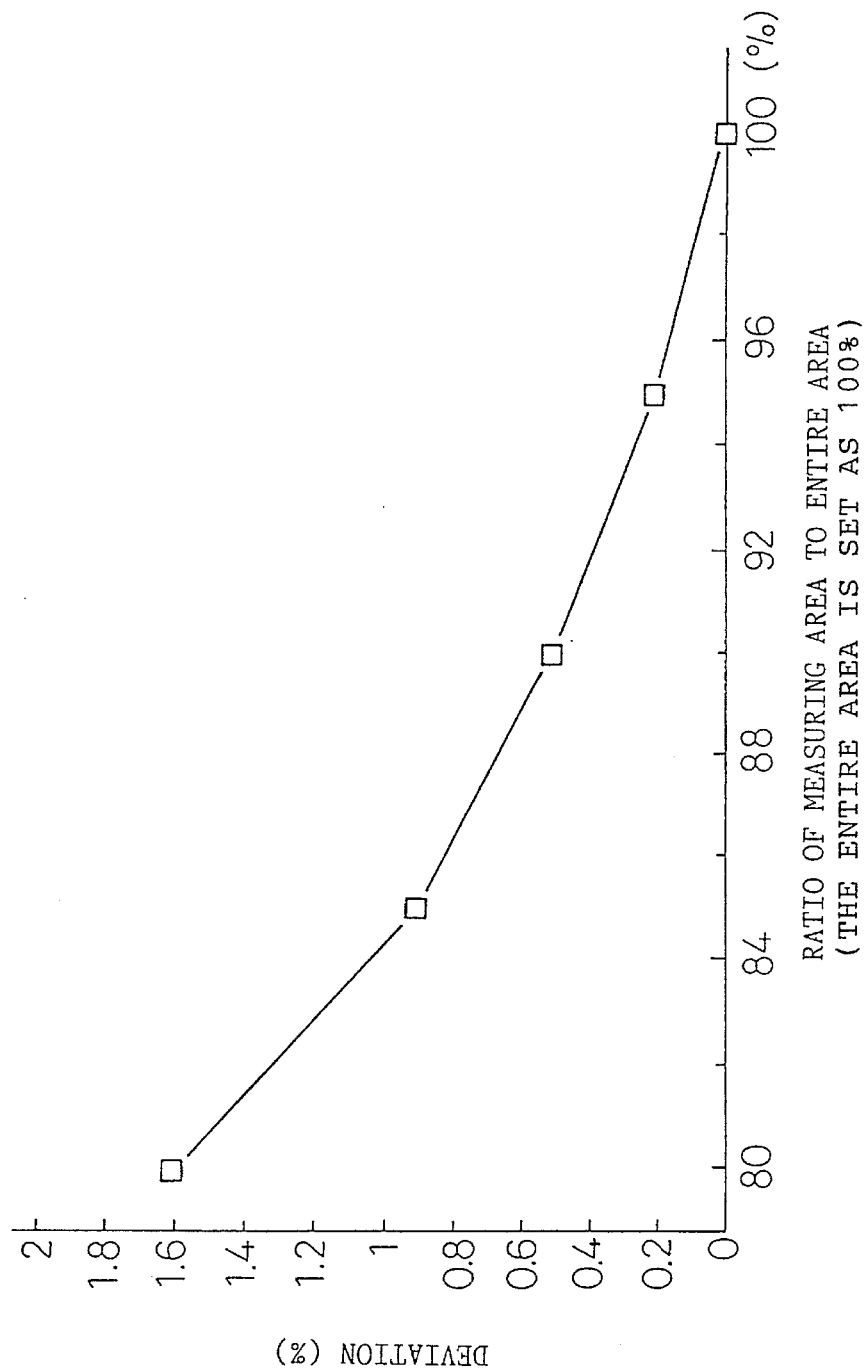
FIG. 23 is a graph showing the deviation of measurable area from a true value (data of all the measuring areas) when a smoothing process in accordance with the present invention is used.

FIG. 23 illustrates the deviation of the mean BMD calculated after rejecting abnormal parameters and CV (coefficient of variance). The accuracy of data can be estimated from FIG. 23.

The configuration of a bone morphometric apparatus in a preferred embodiment for carrying out the bone morphometric method may be similar to that of the bone morphometric apparatus shown in FIG. 7.

Referring again to FIG. 7, an automatic read unit 1 comprises a linear image sensor (CCD) for detecting signals, i.e., the intensity of light transmitted through a radiograph formed on an X-ray film and corresponding to the density of the radiograph formed on the X-ray film, extended perpendicularly to a film feed direction, a linear light source (LED) for irradiating the X-ray film with light from above or from below the same, a rod lens for focusing transmitted light transmitted through the radiograph formed on the X-ray film on the linear sensor, and a film moving device for moving the X-ray film minutely with a stepping motor.

A film feed controller, i.e., a control means, controls the movement of the x-ray film to detect transmitted light transmitted through only a specified region on the x-ray film and makes the x-ray film move intermittently at a given speed. A CCD driver has a control function to read data stored in the CCD at predetermined time. An LED controller is a luminous intensity adjusting means for adjusting the luminous intensity of light emitted by a light source according to the level of density of the radiograph formed on the x-ray film.

Means for specifying two points on the head of the sample bone and two points on the shaft of the sample bone in an image of the sample bone may be a CRT, i.e., an image display means, for displaying the image of the sample bone, and a keyboard or a light pen, i.e., a point specifying means for specifying points in the image displayed on the CRT. A means for determining the bone axis by connecting the middle point between the two points on the head of the sample bone and the middle point between the two points on the shaft is, for example, a computer means comprising a ROM for storing processing programs, and a RAM for arithmetic operation and temporary data storage.

A system including a reference measuring line setting means for setting a reference measuring line perpendicularly intersecting the bone axis at a point at a given distance from one of or the middle point between the two points on the head of the sample bone, a pattern forming means for forming patterns of the quantity of transmitted radiations transmitted through the sample bone along the reference measuring line, or a single or a plurality of measuring lines near the reference measuring line, and a measuring means for processing the patterns by predetermined arithmetic operations for the measurement of the sample bone is, for example, a computer means comprising a ROM for storing the contents of the process, a RAM for arithmetic operation and temporary data storage, and a CPU.

In a pattern of the quantity of transmitted light determined by irradiating an x-ray film having both an image of the sample bone and that of a standard matter with light and detecting transmitted light, the density of the image of the sample bone can be converted into density data expressed in terms of the thickness of a standard matter by comparing the quantity of transmitted light transmitted through the image of the sample bone with the quantity of transmitted light transmitted through the image of the standard matter, which reduces errors attributable to the variation of the density of the images formed on the x-ray film dependent on x-raying conditions. The standard matter is a wedge-shaped standard block having continuously gradate thickness or a stepped standard block having thickness varying in steps of 1 mm. When the wedge-shaped standard block is used, the quantity of transmitted light transmitted through the image of the sample bone is compared directly with that of transmitted light transmitted through the image of the wedge-shaped standard block to convert the quantity of transmitted light into data expressed by the thickness of the wedge-shaped standard block. When converting the quantity of transmitted light transmitted through the image of the sample bone into data expressed by the respective thicknesses of steps of the stepped standard block and the quantity of light transmitted through the image of the sample bone corresponds to a thickness between those of the adjacent steps of the stepped standard block, a thickness corresponding to the quantity of transmitted light transmitted through the image of the sample bone is determined by linear interpolation or spline interpolation. These arithmetic operations are carried out by the aforesaid computer means comprising the ROM, the RAM and the CPU.

The data read by the automatic read unit 1 shown in FIG. 7 is stored in an image storage device comprising, as principal components, an image I/O unit of the data processing unit 2, and an image memory. The stored image data is displayed in an enlarged pattern of the sample bone by an image display means comprising, as principal components, a CRTC and a CRT.

An arithmetic means included in the bone morphometric apparatus of the present invention may be of any type, provided that the arithmetic means is capable of determining a predetermined measuring region in the image of the sample bone stored in the image storage means with reference to the reference points specified by the point specifying means, and of converting the image data of the predetermined region in the image of the sample bone into data expressed by the thickness of the standard matter by using the stored data on the respective images of the sample bone and the standard matter and of processing the data for bone measurement. A computer means, such as a microcomputer, comprising a ROM for storing arithmetic programs for bone measurement, and a RAM for arithmetic operation and temporary data storage is an example of the arithmetic means.

Figure 24:
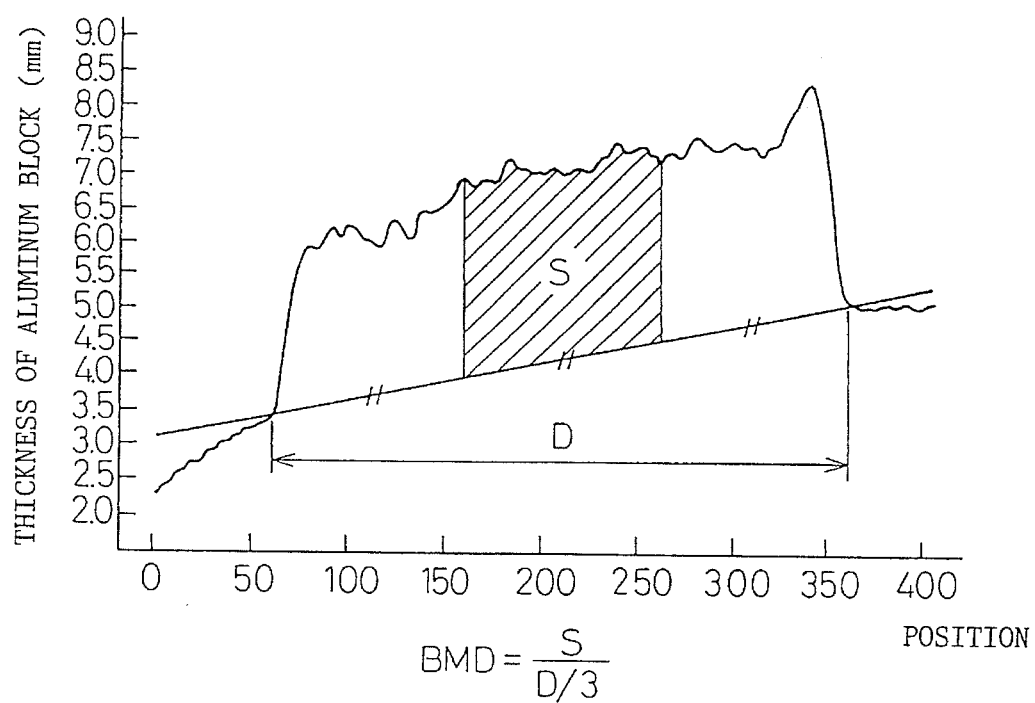
FIG. 24 is a graph showing measured data on the radius measured by the present invention.
Figure 25:
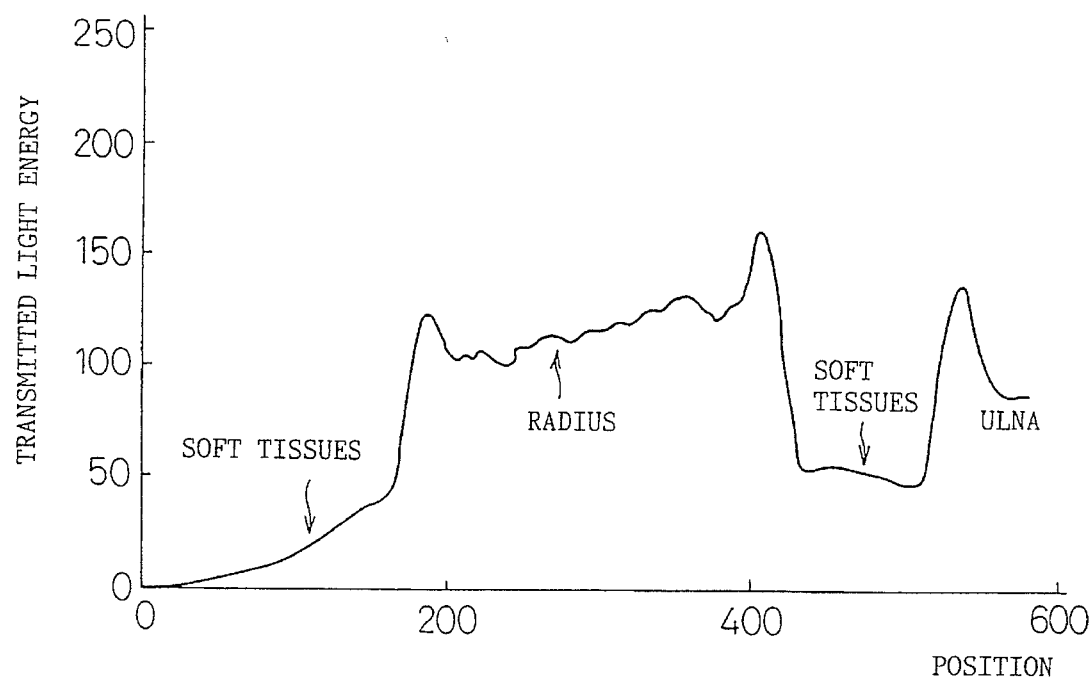
FIG. 25 is a graph showing a pattern of the quantity of transmitted radiations transmitted through the radius, by way of example.
Figure 26:
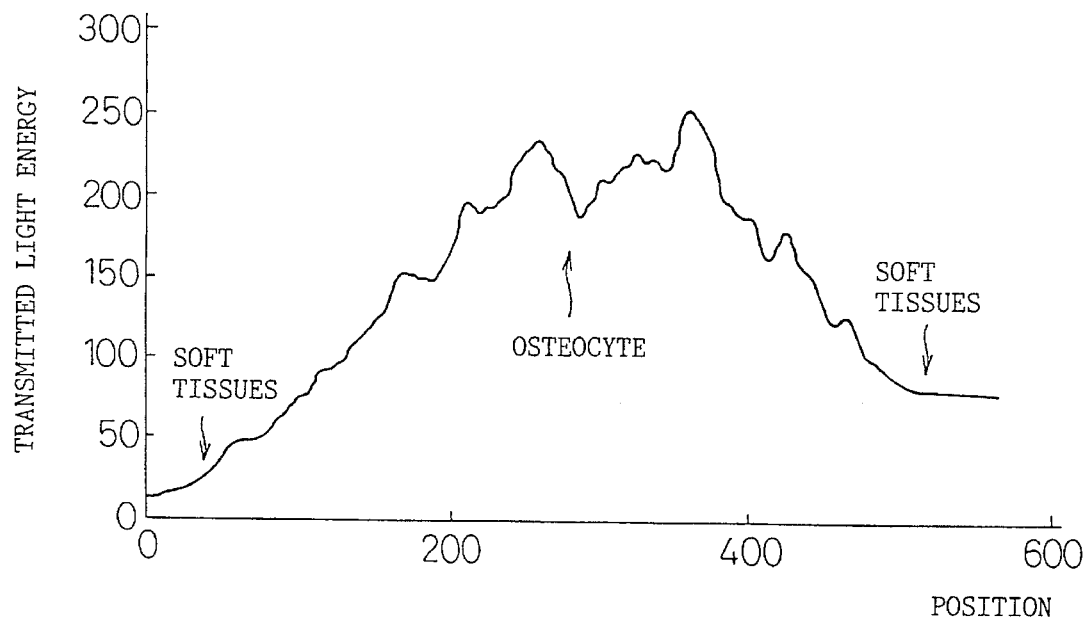
FIG. 26 is a graph showing a pattern of the quantity of transmitted radiations transmitted through a bone rich with cancellate bone.
Figure 29:
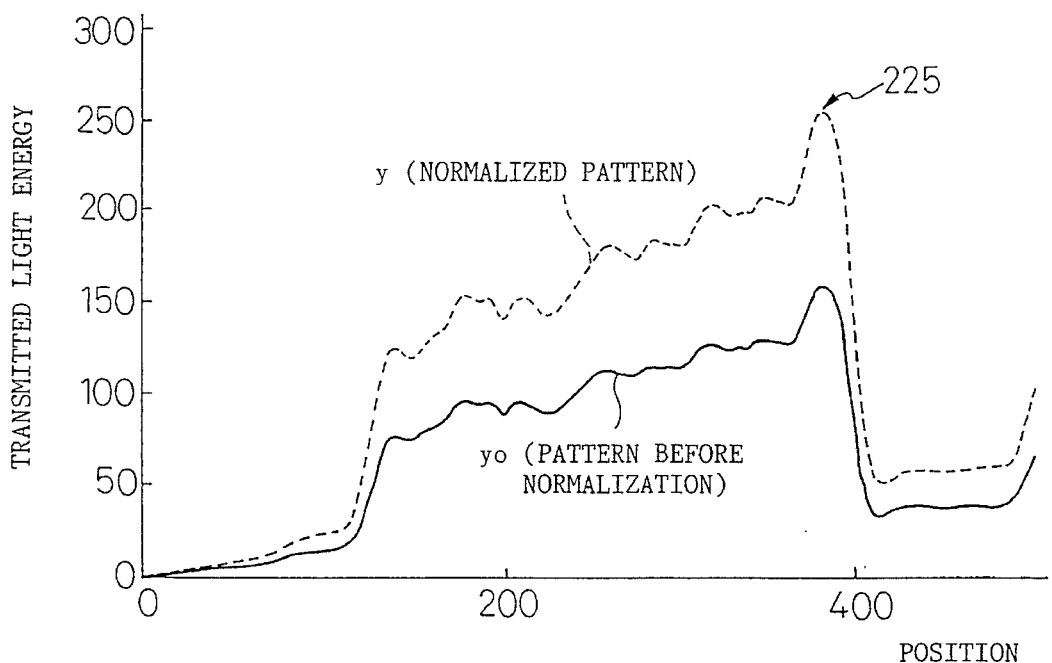
FIG. 29 is a graph of assistance in explaining a procedure for normalizing a pattern of the quantity of transmitted radiations, included in a bone morphometric method in accordance with the present invention.

FIG. 24 shows a pattern representing the stored image data acquired along the given measuring line at the distal end of the radius and expressed by the thickness of the standard matter to illustrate the contents of arithmetic operations concretely, in which a bone density distribution in a region along the bone width D is shown and the bone width D and the BMD are used as parameters.

In the bone morphometric apparatus in this embodiment, the data processing unit 2 of FIG. 7 includes a pattern smoothing means for obtaining a smoothed pattern, a means for obtaining a plurality of parameters for bone measurement and measuring means for processing the plurality of parameters for measuring the sample bone. More concretely, the data processing unit 2 includes a microcomputer comprising a MPU, a ROM for storing processing programs and a RAM for arithmetic operation and temporary data storage.

Although this embodiment employs the X-ray film, the present invention is readily applicable to an apparatus that forms an image of a sample bone on an X-ray image sensor by irradiating the sample bone with X-rays.

FIG. 10 systematically illustrates the construction and arrangement of the bone morphometric apparatus for carrying out a series of operations from an X-raying operation to a bone measuring operation. An image forming apparatus that irradiates an X-ray image sensor directly together with a sample bone with X-rays emitted by an X-ray source 20 uses an imaging plate 21 instead of a film cassette containing an X-ray film, which is employed in the conventional roentgenography, and reads X-ray information recorded on the imaging plate 21 by irradiating the X-ray information with a laser beam emitted by a laser light emitting means 22 and by detecting the laser beam by an optical detector 23 to obtain light signals representing the intensities of X-rays. An image processing unit 25 subjects photoelectric information read from the imaging plate to A/D conversion to obtain an X-ray image 24 of the sample bone, and the X-ray image 24 is processed for bone measurement by the foregoing bone morphometric method and the foregoing bone morphometric apparatus of the present invention.

The bone morphometric method and the bone morphometric apparatus in this embodiment reduce the effect of, for example, dislocation of the reference points 13, 14, 15 and 16 shown in FIG. 8 on bone measurement and are capable of achieving highly repeatable bone measurement. Furthermore, the bone morphometric method and the bone morphometric apparatus in this embodiment eliminate abnormal measured data to enhance the accuracy and repeatability of bone measurement. This embodiment is suitable particularly for measuring cancellate bones.

A further embodiment of the present invention will be described hereinafter.

Generally, when measuring only a sample bone having bone and soft tissues, such as the second metacarpus, the distal end of the radius or the heel bone, by using a pattern of the quantity of transmitted radiations, the sample bone has a peculiar distribution of the soft tissues around the same, and different persons (different body weights) have different distributions of the soft tissues. Therefore the influence of soft tissues must be corrected.

A correcting method used by this embodiment will be described below. Referring to FIGS. 28A through 28C, two boundary points on the boundary between the osteocyte and the soft tissues are determined in a pattern of the quantity of transmitted radiation (which is also called "transmitted radiation energy pattern", and see FIG. 28B) determined from the quantity of transmitted light measured by irradiating a radiograph of a sample bone shown in a sectional view in FIG. 28B formed on an X-ray by irradiating the sample bone with X-rays with light and detecting transmitted light transmitted through the radiograph, the pattern of the quantity of transmitted radiation is divided by a line interconnecting the two boundary points into an upper part being a pattern of the quantity of transmitted radiation transmitted through the osteocyte and a lower part being a pattern of the quantity of transmitted radiation transmitted through the soft tissues. The pattern of the soft tissues approximated by the line interconnecting the two boundary points is used for correcting the influence of the soft tissues. The pattern of the soft tissues is subtracted from the approximated pattern of the quantity of transmitted radiation to obtain a corrected pattern of the quantity of transmitted radiation transmitted through the sample bone proper (FIG. 28C). A curved line or a straight line is used depending on the distribution of the thickness of the soft tissues surrounding the sample bone. For example, when the sample bone is the second metacarpus or the distal end of the radius, it is preferable to use a straight line because the thickness of the soft tissues corresponding to the bone in the pattern of the quantity of transmitted radiation is substantially uniform.

A method of determining parameters D and BMD will be described below.

Bone width D is determined on the basis of the distance between the two boundary points on the boundary between the osteocyte and the soft tissues. BMD (bone mineral density) is determined by converting the corrected pattern into pattern data expressed by the thickness of the standard matter on the basis of the thickness of the standard matter and the quantity of transmitted light, calculating the area S of the entire region along the bone width or a region of a width x measured on the opposite sides of the middle of the bone width, and dividing the area S by the width of the region, i.e., the bone width D or the width x, as shown in FIGS. 28D and 28E.

Therefore, the boundary between the osteocyte and the soft tissues must be correctly determined to measure the sample bone correctly and accurately, because the dislocation of the boundary points causes, for example, BMD to change.

A method of determining the boundary between the osteocyte and the soft tissues to be carried out by this embodiment will be described in detail. As shown in FIG.

29, values of the pattern of the quantity of transmitted radiation are normalized by the representative of the pattern. Generally, different portions of a sample bone or different persons have different patterns of transmitted radiation energy, and the level of the pattern is dependent also on the density of the radiograph formed on an X-ray film and the luminous intensity of light for irradiating the radiograph formed on an X-ray film. Normalization of the values of the pattern is effective in determining osteocyte and soft tissues and determining given conditions. For example, when carrying out 8-bit A/D conversion, it is preferable to enlarge the values of the pattern so that a maximum corresponding to the maximum value of the pattern is 255.

A method of determining a point as a first neighborhood point where the gradient changes sharply or a neighborhood point near the first neighborhood point will be described below to determine boundary points on the boundary between the sample bone and the soft tissues. Generally, a point on a mathematically continuous pattern where gradient changes sharply can be readily determined by differentiation of the second order. This embodiment found that a point where gradient changes sharply or a neighborhood point near such a point can be correctly determined for a discrete pattern by a digital processing system using a second difference and/or the product of a second difference and a first difference.

Figure 30:
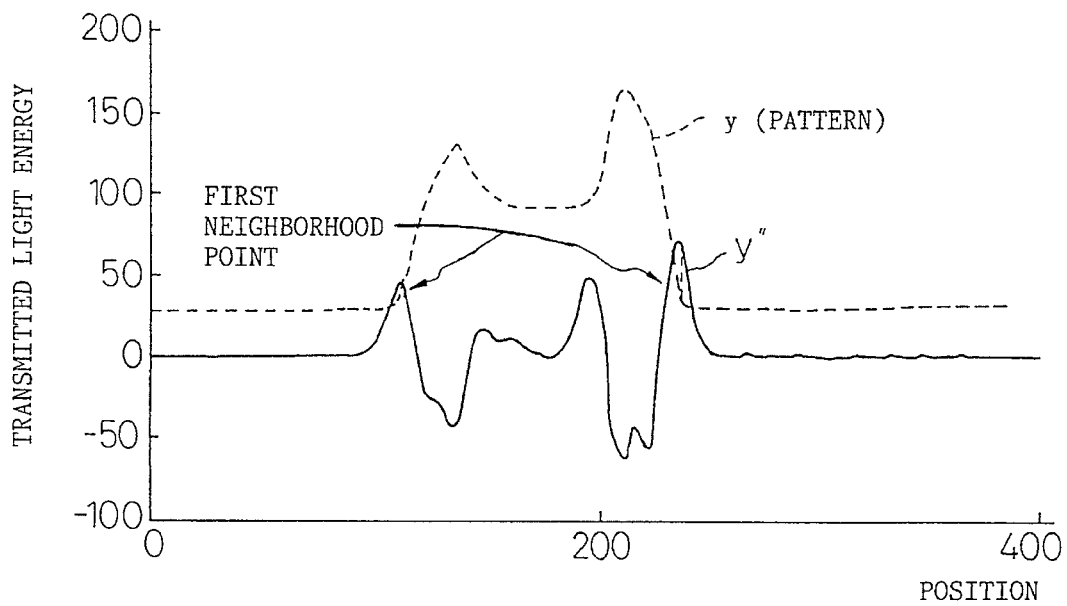
FIG. 30 is a graph of assistance in explaining a procedure for determining a first neighborhood point by using a second difference for boundary point.

In a pattern as shown in FIG. 30 formed by measuring a cortical bone in which the change in the soft tissues is small and the osteocyte and the soft tissues can be exactly discriminated from each other, peaks can be readily found by searching for the second difference y" of a region of the transmitted radiation energy pattern corresponding to the boundary points on the boundary between the osteocyte and the soft tissues or to the vicinity of the boundary point from left to right for a peak y" of a value not less than a given value and searching the same from right to left for a peak y" of a value not less than a given value.

Figure 31:
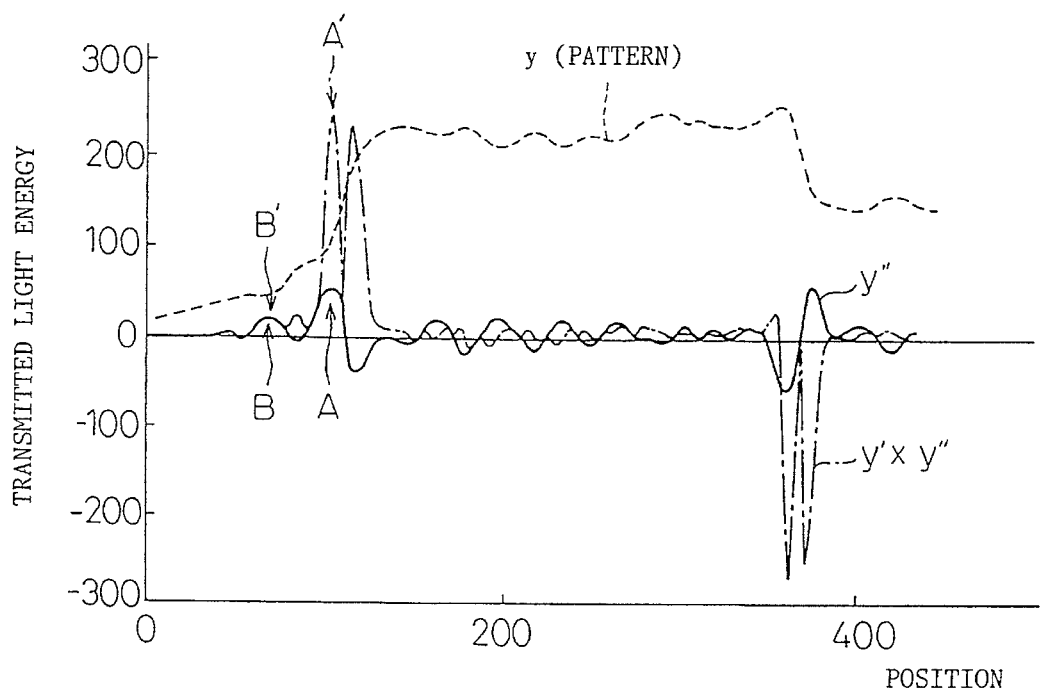
FIG. 31 is a graph of assistance in explaining a procedure for determining a first neighborhood point by using a first difference and a second difference, included in a bone morphometric method in accordance with the present invention.

However, in a pattern as shown in FIG. 31 formed by measuring a bone in which the change in the soft tissues is large, the difference between a peak A corresponding to the boundary point on the boundary between the osteocyte and the soft tissues or the vicinity of the boundary point, and a peak B due to a change in the soft tissues is small.

Accordingly, it is impossible to detect the boundary point or the vicinity of the boundary point correctly in different patterns under fixed conditions.

The inventors of the present invention found, through intensive studies to solve such a problem, that it is preferable to use the product of the second difference and the first difference and have made the present invention. The product of the first difference and the second difference is expressed mathematically by:

$$y'(x_i)y''(x_i)=[y(x_{i+k/2})-y(x_{i-k/2})]\{[y(x_{i+k})-y(x_i)]-[y(x_i)-y(x_{i-k})]\}$$

where k=2, 4, 6, . . . or 2n dependent on the transmitted radiation energy pattern.

Thus, in the example shown in FIG. 31, only the point where the gradient changes sharply can be emphasized, the difference between the peak A' corresponding to the desired boundary point or the neighborhood point and the peak B' due to the soft tissues as disturbance is five times the difference determined by the method using only the second difference, and the boundary point or the neighborhood point can be readily determined.

Figure 32:
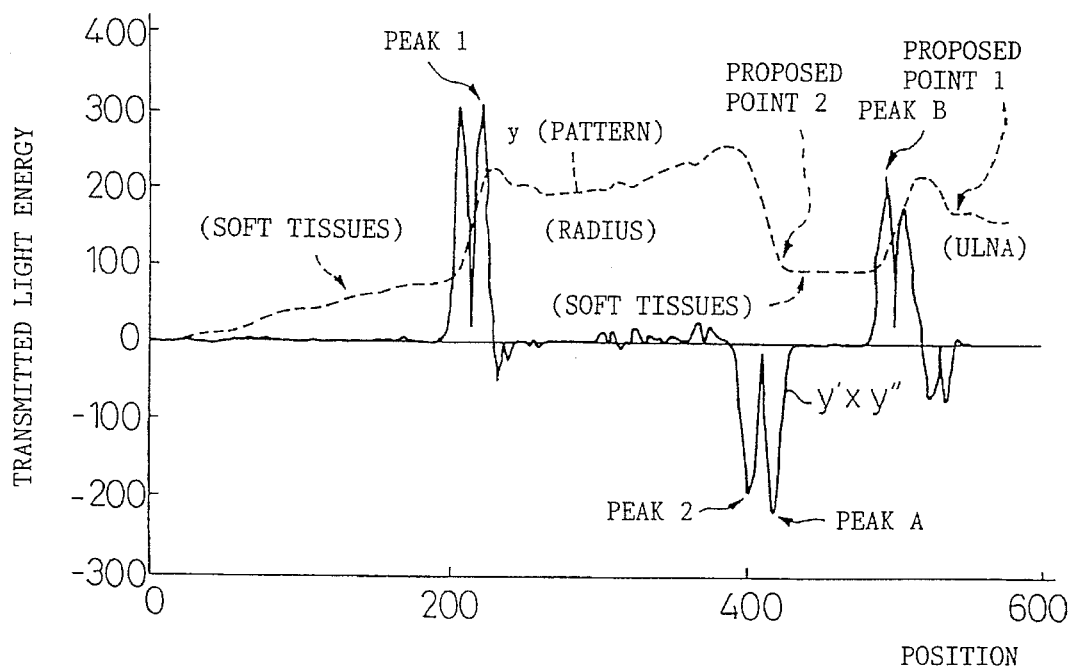
FIG. 32 is a graph of assistance in explaining a procedure for determining a first neighborhood point included in a bone morphometric method in accordance with the present invention.

A case where other bones lie around the sample bone will be described below. First, a proposed point on the sample bone must be selected from among the plurality of proposed points determined by the method using the product of the first difference and the second difference, and the second difference. For example, when measuring the radius as shown in FIG. 32, a proposed point 1 (ulna) and a proposed point 2 (radius) are determined. Since the level of the soft tissues is lower than that of the osteocyte, two proposed points on the sample bone can be selected by selecting a transmitted radiation energy pattern of the lower level. Thus, even though other bones lie around the sample bone and measuring lines extend onto the sample bone, the sample bone can be measured without adjusting the lengths of the measuring lines.

As mentioned above, although the first neighborhood point (proposed point) is determined by using the second difference and/or the product of the first difference and the second difference when determining the boundary between the osteocyte and the soft tissues, a point where the gradient changes sharply, from a discrete pattern (digital pattern), it was found that the proposed point is dislocated from a correct boundary point on the boundary between the osteocyte and the soft tissues owing to the number of the differences or the transmitted radiation energy pattern.

A first method uses the proposed point ($P_1$ in FIG. 33) for correcting the influence of the soft tissues on a transmitted radiation energy pattern of the osteocyte and the soft tissues. However, the measurement of BMD contains an error and, in some cases, accurate measurement cannot be achieved. The value of the error contained in BMD calculated for the entire bone width by this method is shown in FIG. 33.

A second method determines a new proposed point on the basis of this proposed point and corrects the influence of the soft tissues on the transmitted radiation energy pattern of the osteocyte and the soft tissues. As illustrated in FIG. 33, the method of determining a new proposed point determines a first regression line near a point where the gradient from the proposed point toward the center of the sample bone, and determines a first regression line in a given region away from the center of the sample bone, and uses the intersection of the regression lines as a new proposed point $P_2$.

Figure 33:
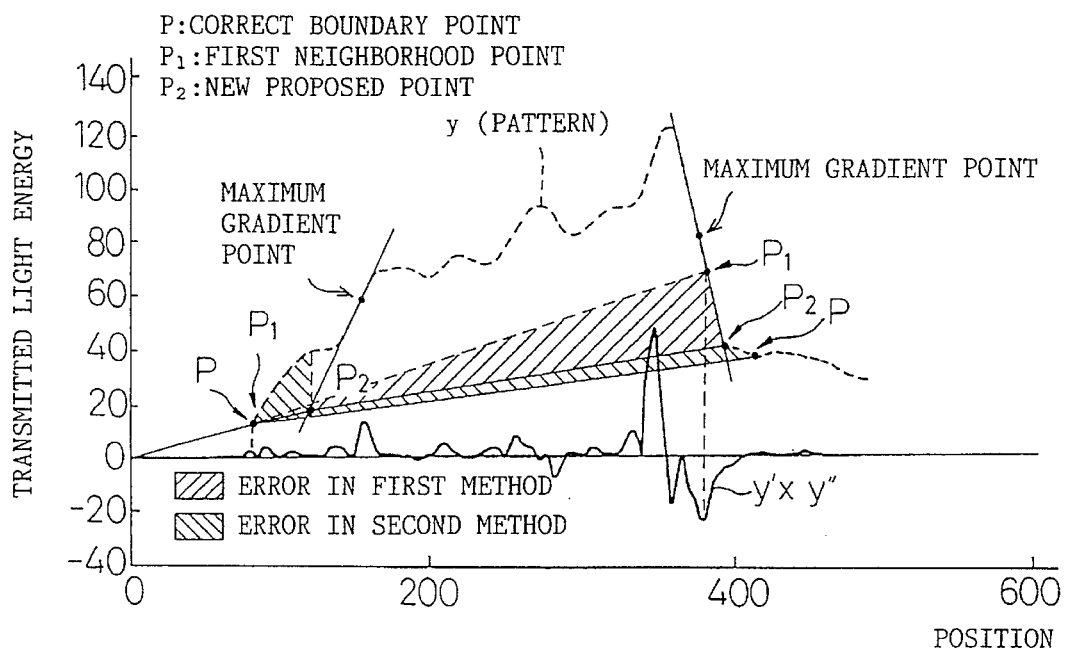
FIG. 33 is a graph of assistance in explaining a procedure for determining a boundary point, included in a bone morphometric method in accordance with the present invention.

As is obvious from FIG. 33, the data processing error in carrying out the second method is smaller than that in carrying out the first method, however, in some cases, the accuracy is not necessarily high enough to determine a correct boundary point. It was found, through further studies to solve such a problem, that the problem can be solved and the data can be measured and processed with a satisfactory accuracy by setting a region of linear regression and repeating the linear regression processing.

Figure 34:
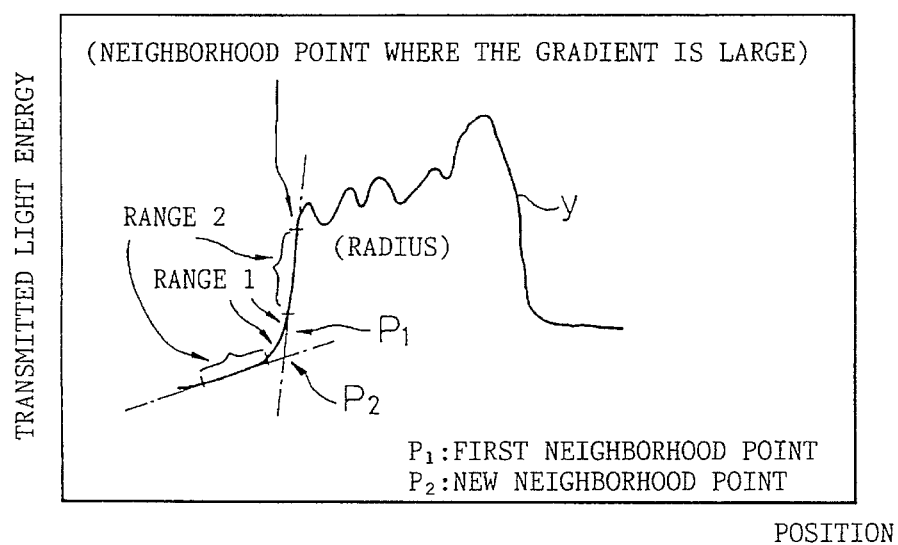
FIG. 34 is a graph of assistance in explaining a procedure for determining a boundary point in accordance with the present invention.

The content of the second method will hereinafter be described in more detail with reference to FIGS. 34 and 35.

The first predetermined ranges 1 to 4 used by the present invention will be explained. Referring to FIG. 34, a predetermined range 1 is determined statistically by using the sample bone and the number of differences when determining a neighborhood point from the transmitted radiation energy pattern of the sample bone. For example, when measuring the distal end of the radius, the preferable number of differences is eleven (sampling intervals of 63.5 µm and sampling length of about 0.7 mm), and a range between neighborhood points where the gradient changes sharply (which corresponds to the peaks 1 and 2 in FIG. 32) is a preferable predetermined range 2, because the determination of a regression line in an inappropriate range (the vicinity of the point where the gradient is a maximum in the second method) can be avoided as shown in the left-hand portion of FIG. 33.

Figure 35:
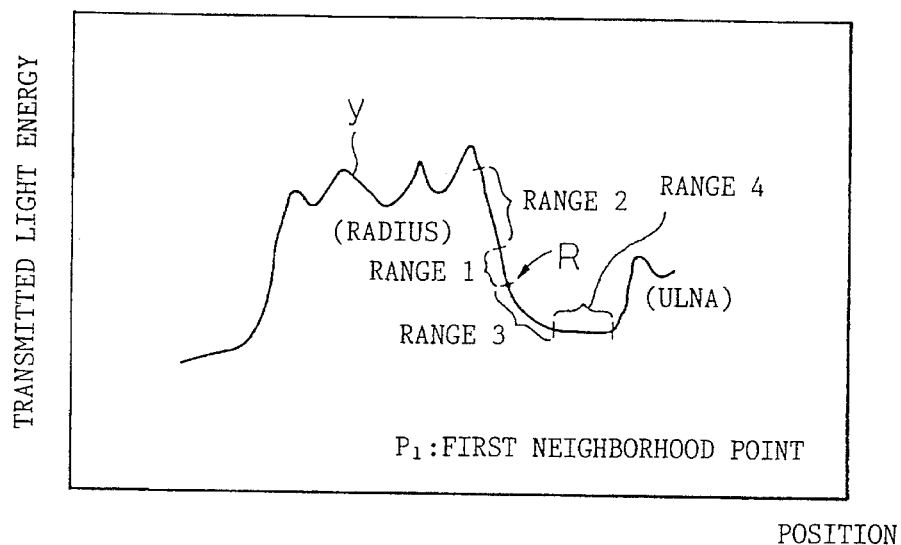
FIG. 35 is a graph of assistance in explaining a procedure for determining a boundary point in accordance with the present invention.

Referring to FIG. 35, when the influence of other bones is significant, it is desirable to determine a regression line in a predetermined range 4 where the gradient changes slightly, because some sample bone or the bones of some persons is surrounded by cartilage and hence the pattern changes gently. The predetermined range 3 is from the neighborhood point to a point where the product of the first difference and the second difference is smaller than a given value. The given value for example, for the distal end of the radius is "1" when both the first difference and the second difference are "11" after the transmitted radiation energy pattern has been normalized. When there are other bones around the sample bone, the predetermined range 4 is determined on the basis of the distance between the radius and the ulna as shown in FIG. 35. If the distance between the radius and the ulna is short, such as 0.5 mm, it is desirable to determine a straight line representing a fixed radiation energy by calculating the mean value of predetermined region 4 of the pattern instead of using a regression line in the predetermined region 4.

Figure 36:
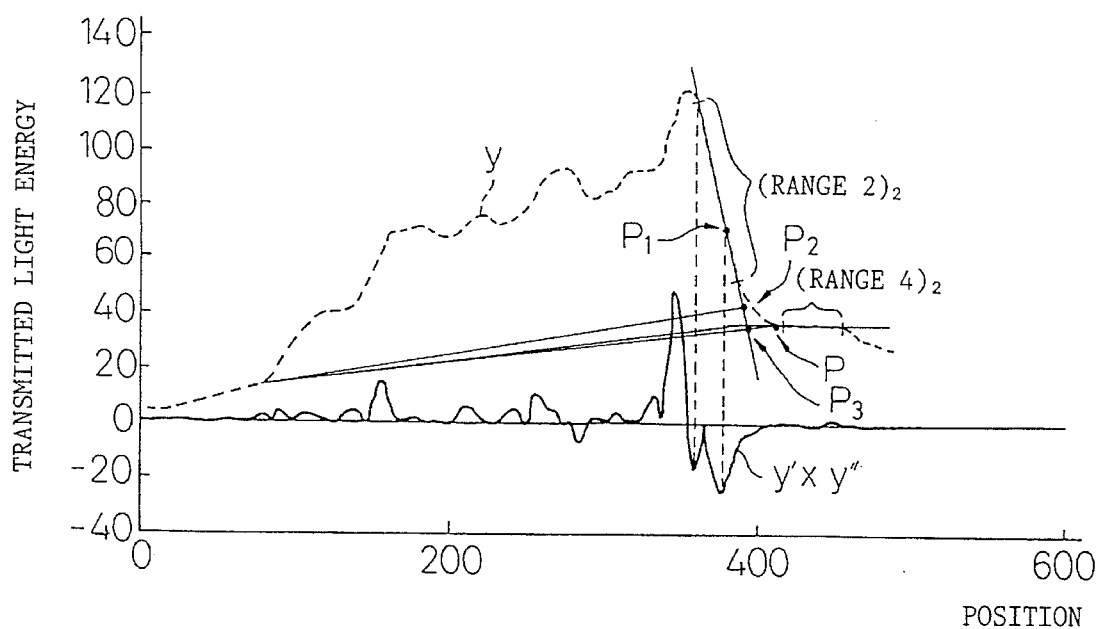
FIG. 36 is a graph of assistance in explaining a procedure for determining a boundary point in accordance with the present invention.

For a pattern in which accuracy cannot be increased sufficiently by one cycle of the foregoing process as shown in FIG. 36, calculation of regression must be repeated several times.

In FIG. 36, a new proposed point $P_2$ is determined from the proposed point $P_1$ by a first cycle of regression by the aforesaid method, and then another new proposed point $P_3$ is determined from the proposed point $P_2$. Thus, the proposed point changes from $P_1$ through $P_2$ and $P_3$ and approaches a correct boundary point P. The number of cycles of the regression process is dependent on the transmitted radiation energy pattern and required measuring accuracy.

The difference between a BMD determined by using a pattern as shown in FIG. 36 for the radius and a BMD determined by manual operation using a supposedly correct boundary point was 34% when the BMD was determined by the first method, 32% when linear regression was carried out once, and was 1.1% when linear regression was repeated twice.

An image input means for providing an image based on the transmitted radiation energy determined by irradiating the sample bone with radiations and detecting transmitted radiations transmitted through the sample bone may be a device that irradiates a radiograph formed on an X-ray film from above or from below the X-ray film with light emitted by a linear light source (LED) and detects light transmitted through the radiograph with a linear sensor (CCD).

A system including a pattern forming means for forming a pattern of the quantity of radiation transmitted through a measuring region in the input image along a measuring line, a pattern correcting means for correcting the pattern to obtain a corrected pattern of the quantity of transmitted radiations by determining two boundary points on the boundaries between soft tissues and the opposite ends of the sample bone in the pattern, and subtracting a region of the quantity of transmitted radiations corresponding to the soft tissues approximated by a line interconnecting the two boundary points from the pattern, and an arithmetic means for measuring the sample bone by using the corrected pattern may be a computer means, such as a microcomputer, including a ROM for storing arithmetic program for controlling arithmetic operations, and a RAM for arithmetic operation and temporary data storage.

Figure 37:
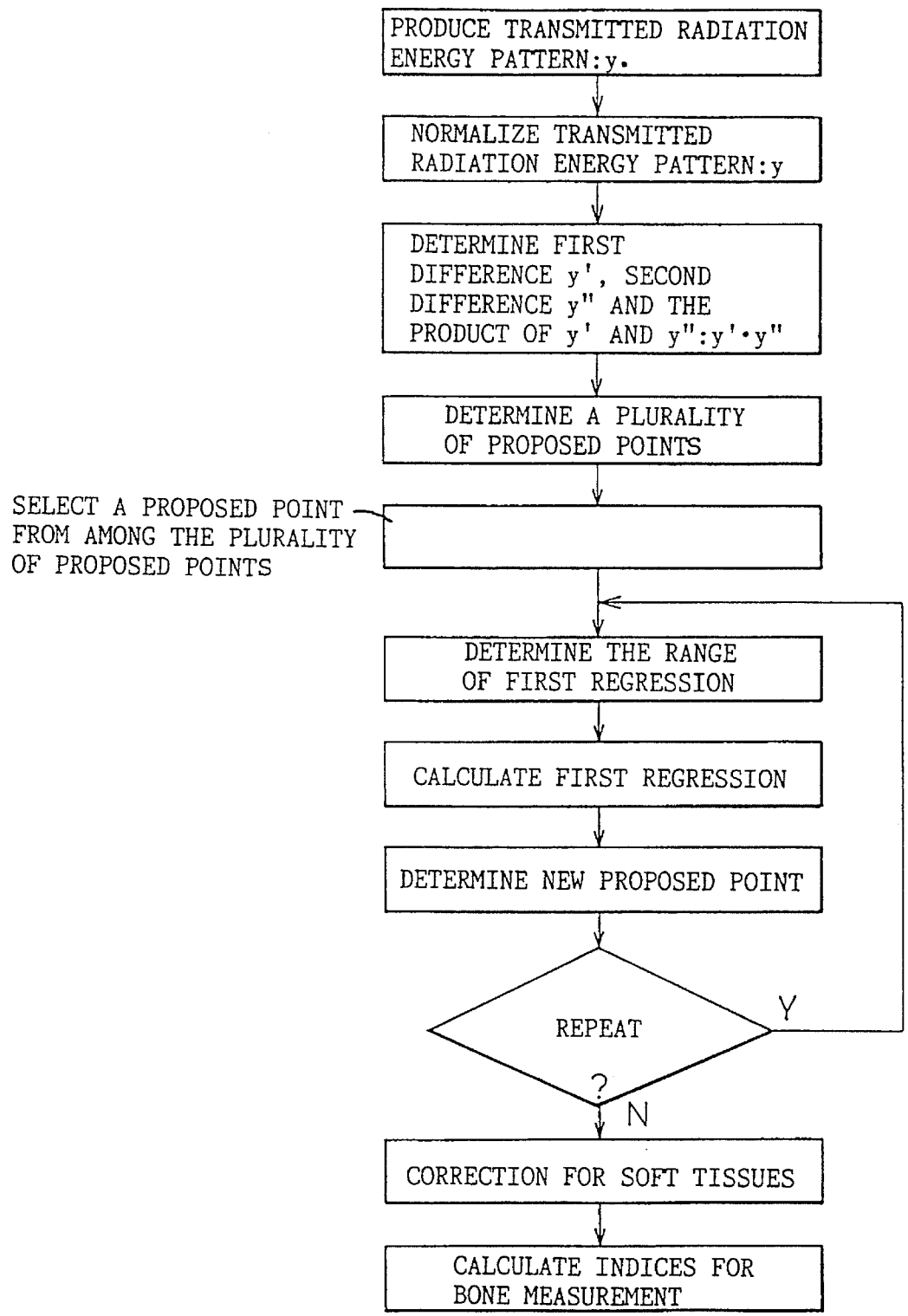
FIG. 37 is a flow chart of a program to be carried out by a bone morphometric method in accordance with the present invention; and, FIG. 38 is a graph of assistance in explaining an image reading procedure included in a bone morphometric method in accordance with the present invention.

FIG. 37 is a flow chart of the bone morphometric method in this embodiment. The bone morphometric apparatus in this embodiment is identical with the foregoing bone morphometric apparatus previously described with reference to FIG. 7. An automatic read unit 11 comprises a linear image sensor (CCD) for detecting signals, i.e., the intensity of light transmitted through a radiograph formed on an X-ray film and corresponding to the density of the radiograph formed on the X-ray film, extended perpendicularly to a film feed direction, a linear light source (LED) for irradiating the X-ray film with light from above or from below the same, a rod lens for focusing the light transmitted through the radiograph formed on the X-ray film on the linear sensor, and a film moving device for moving the X-ray film minutely with a stepping motor.

A film feed controller, i.e., a control means, controls the movement of the X-ray film to detect light transmitted through only a specified region on the X-ray film and makes the X-ray film move intermittently at a given speed. A CCD driver has a control function to read data stored in the CCD at predetermined times. An LED controller is a light intensity adjusting means for adjusting the intensity of light emitted by a light source according to the level of density of the radiograph formed on the X-ray film.

Figure 38:
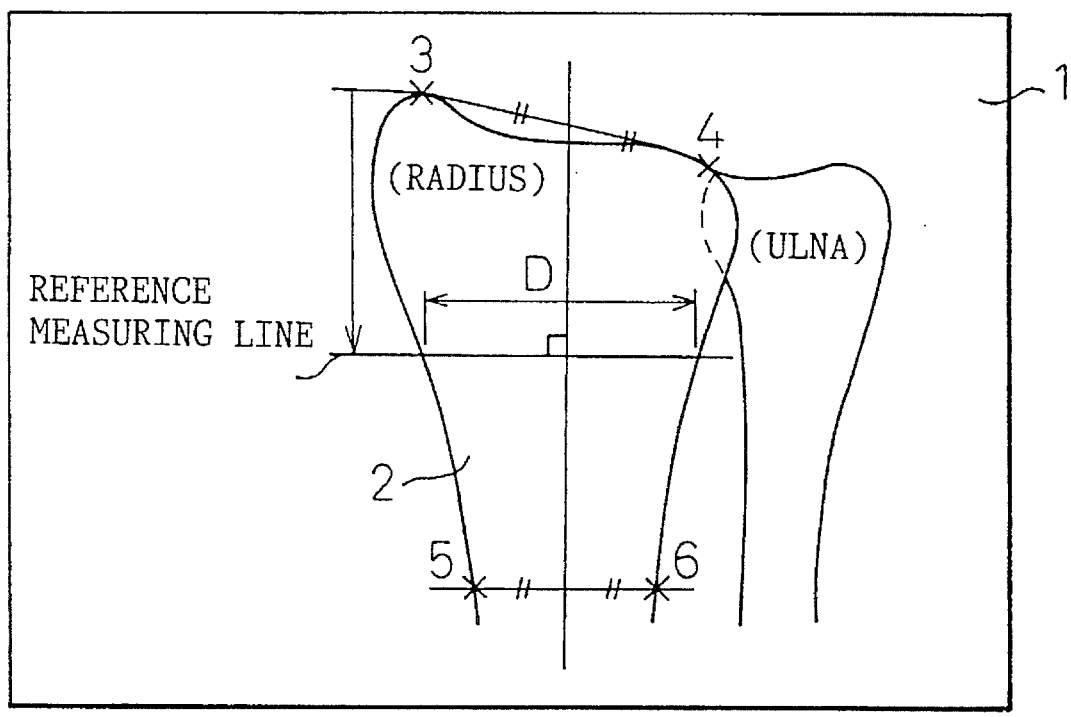

FIG. 38 illustrates an enlarged image of the radius displayed on the CRT, i.e., an image display means, included in a data processing unit 12 of the bone morphometric apparatus of FIG. 7. Shown in FIG. 38 are a screen 1, the radius 2, and reference points 3, 4, 5 and 6 necessary for bone measurement. It is preferable for ensuring satisfactory positional repeatability to use a reference measuring line determined by connecting the middle point between the reference points 3 and 4 and the middle point between the reference points 5 and 6, and drawing a line perpendicular to the line connecting the middle points at a point at a given distance from the reference point 3. A point specifying means for specifying the reference points may be a cursor control means, a light pen input means or a touch panel input means.

Data read by the automatic read unit 11 of the bone morphometric apparatus of FIG. 7 is stored in an image storage device comprising, as principal components, an image I/O unit of the data processing unit 12 and an image memory. The stored image data is displayed in an enlarged pattern of the sample bone by an image display means comprising, as principal components, a CRTC and a CRT.

An arithmetic means included in the bone morphometric apparatus of the present invention may be of any type, provided that the arithmetic means is capable of determining a predetermined measuring region in the image of the sample bone stored in the image storage device with reference to the reference points specified by the point specifying means, and of processing the stored image data of the sample bone in the predetermined measuring region by arithmetic operations. A computer means, such as a microcomputer, comprising a ROM storing arithmetic programs for bone measurement, and a RAM for arithmetic operation and temporary data storage is an example of the arithmetic means.

Although the above-mentioned example of this embodiment employs X-ray film, the present invention is readily applicable to an apparatus that forms an image of a sample bone on an X-ray image sensor by irradiating the sample bone with X-rays.

A system of the bone morphometric apparatus in this embodiment for carrying out a series of operations from an X-raying operation to a bone measuring operation may be the system previously described with reference to FIG. 10.

An image forming apparatus that irradiates an X-ray image sensor directly together with a sample bone 19 with X-rays emitted by an X-ray source 20 uses an imaging plate 21 instead of a film cassette containing an X-ray film, which is employed in the conventional radiography. X-ray information recorded on the imaging plate 21 is read by irradiating the X-ray information with a laser beam emitted by a laser light emitting means 22 and by detecting the laser beam by an optical detector 23 to obtain light signals proportional to the intensities of the X-rays. An image processing unit 25 subjects photoelectric information read from the imaging plate to A/D conversion to obtain an X-ray image 24 of the sample bone, and the X-ray image is processed for bone measurement by the bone morphometric method and the bone morphometric apparatus in this embodiment.

The present invention includes a bone morphometric apparatus that uses an image represented by the quantity of transmitted gamma rays, obtained by irradiating a sample bone with gamma rays and detecting transmitted gamma rays by photon absorptiometry.

The bone morphometric method and the bone morphometric apparatus in this embodiment are capable of automatically and correctly detecting the boundary between osteocyte and soft tissues in reading an image and hence is capable of readily and accurately measuring bones rich in cancellate bones.

Although the present invention has been described in its specific embodiments, many changes and variations are possible therein in the light of above technical teachings without departing from the scope and spirit of the invention.

We claim:

1. A bone morphometric method using a radiograph of a sample bond produced by radiography to measure the sample bone, said bone morphometric method comprising the steps of:

(i) determining a bone axis in a region of interest by specifying two points on the head of the sample bone and two points on the shaft of the sample bone, and interconnecting the middle point between the former two points and the middle point of the latter two points;

(ii) setting a reference measuring line perpendicular to the bone axis and intersecting the bone axis at a point at a given distance from any one of the two points on the head of the sample bone and the middle point between the same two points;

(iii) producing a pattern or patterns of the quantity of radiation transmitted through the radiograph of the sample bone along the reference measuring line, or one or a plurality of measuring lines extending near the reference measuring line; and (iv) processing data representing the pattern or the patterns by arithmetic operations for the morphometric measurement of the sample bone.

2. The bone morphometric method according to claim 1, wherein the sample bone is the radius, and the given distance is a length expressed by the length of the metacarpus.

3. The bone morphometric method according to claim 1, wherein said method further comprises the steps of:

obtaining an image by irradiating the radiograph of the sample bone and a standard matter formed on an X-ray film with light and detecting the quantity of light transmitted through the radiograph; and producing a pattern or patterns by converting the pattern or patterns of the quantity of radiation transmitted through the radiograph of the sample bone into data expressed by the thickness of the standard matter on the basis of the relation between the thickness of the standard matter and the quantity of transmitted light.

4. The bone morphometric method according to claim 1, wherein said method further comprises the steps of:

producing a smoothed pattern by smoothing a group of patterns wherein said group of patterns is a part of a plurality of a group of patterns produced by the step for producing the pattern or patterns of the quantity of radiation transmitted through the radiograph of the sample bone along one or a plurality of measuring lines, by a pattern smoothing operation;

repeating the pattern smoothing operation to produce a plurality of smoothed patterns by smoothing other groups of patterns;

obtaining a plurality of groups of parameters for bone measurement by processing the plurality of smoothed patterns by predetermined arithmetic operations; and processing the plurality of groups of parameters under predetermined conditions to measure the sample bone.

5. The bone morphometric method according to claim 4, wherein said method further comprises the step of:

obtaining the plurality of groups of parameters under the predetermined conditions by comparing each group of parameters with given standard values, eliminating the groups of parameters deviating from the standard values by given values from the standard values, and calculating the mean of the parameters of the remaining groups of parameters.

6. The bone morphometric method according to claim 5, wherein the standard values relate to bone width in the smoothed patterns.

7. The bone morphometric method according to claim 4, wherein the method further comprises the steps of:

specifying two boundary points on the boundary between the osteocyte and the soft tissues at each of the opposite ends of the sample bone for each of the plurality of smoothed patterns;

obtaining a corrected pattern representing the quantity of radiation transmitted through the sample bone proper by subtracting a pattern of the quantity of radiation transmitted through the soft tissues approximated by a line interconnecting the two boundary points from each smoothed pattern.

8. A bone morphometric method according to claim 7, wherein at least one of the two boundary points specified on the boundary between the osteocyte and the soft tissues on the opposite ends of the sample bone in each of the plurality of smooth patterns is specified by the steps of:

specifying a first neighborhood point in each of the smoothed patterns, determining an inner first regression line in a given range (2) skipping by a given range (2) from the first neighborhood point toward the center of the sample bone, determining an outer first regression line in a given range (4) skipping a given range (3) from the first neighborhood point away from the center of the sample bone, determining a second neighborhood point at the intersection of the inner first regression line and the outer first regression line, and repeating the foregoing steps until a new neighborhood point, meeting given conditions, is determined.

9. The bone morphometric method according to claim 8, wherein a second difference and/or the product of the second difference and a first difference in each smoothed pattern is used for determining the first neighborhood point.

10. The bone morphometric method according to claim 4, wherein the method further comprises processing only a portion of the pattern corresponding to a predetermined local region determined on the basis of the bond width of the sample bone by the predetermined arithmetic operations for the measurement of the sample bone.

11. The bone morphometric method according to claim 10, wherein the predetermined local region determined on the basis of the bone width of the sample bone is a region equally extending on the opposites sides of the middle of the bone width of the sample bone and corresponding to the cancellate bone.

12. A bone morphometric apparatus using a radiograph of a sample bone formed by radiography, said bone morphometric apparatus comprising:

(i) means for determining a bone axis of said sample bone by specifying two points on the head of the sample bone and two points on the shaft of the sample bone in a region of interest in an image of the sample bone, and interconnecting the respective middle points of lines connecting the former two points and the latter two points;

(ii) means for setting a reference measuring line perpendicularly intersecting said bone axis at a point at a given distance from any one of the two points on the head of the sample bone and the middle point between the same two points;

(iii) means for producing a pattern or patterns of the quantity of radiation transmitted through the radiograph of the sample bone along the reference measuring line, or one of a plurality of measuring lines extending near the reference measuring line; and (iv) means for processing the pattern or the patterns by predetermined arithmetic operations.

13. The bone morphometric apparatus according to claim 12, wherein the means for processing the pattern of the patterns by the predetermined arithmetic operations is capable of processing the pattern or the patterns only in a predetermined local region determined on the basis of the bone width of the sample bone by arithmetic operations for the measurement of the sample bone.

14. The bone morphometric apparatus according to claim 12, wherein the means for processing the pattern or the patterns by the predetermined arithmetic operations for measuring the sample bone comprises:

(i) means for producing a smoothed pattern by smoothing a group of patterns wherein said group of patterns is a part of a plurality of a group of patterns produced by the means for producing the pattern or patterns of the quantity of radiation transmitted through the radiograph of the sample bone along the one or a plurality of measuring lines, by carrying out a pattern smoothing procedure to smooth a group of patterns and then repeating the pattern smoothing procedure for other groups of patterns to obtain a plurality of smoothed patterns;

(ii) means for obtaining groups of parameters necessary for bone measurement by processing the plurality of smoothed patterns by predetermined arithmetic operations; and (iii) arithmetic means for processing the groups of parameters by predetermined arithmetic operations for the measurement of the sample bone.

15. The bone morphometric apparatus according to claim 12, wherein the means for processing the pattern or patterns by the predetermined arithmetic operations for the measurement of the sample bone comprises:

(i) means for producing a corrected pattern for the quantity of radiation transmitted by the sample bone proper by specifying two boundary points on the boundary between the osteocyte and the soft tissues on the opposite ends of the sample bone in each of a plurality of patterns produced by the means for producing the pattern or patterns of the quantity of radiation transmitted through the radiograph of the sample bone along the one or a plurality of measuring lines, and subtracting a pattern of the quantity of radiation transmitted through the soft tissues approximated by a line interconnecting the two boundary points from the pattern; and (ii) arithmetic means for processing the corrected pattern by arithmetic operations for the measurement of the sample bone.

16. A bone morphometric method using a radiograph of a sample bone to measure the sample bone, said bone morphometric method comprising the steps of:

measuring a pattern or a plurality of patterns of the quantity of radiation transmitted through the sample bone produced along one or a plurality of measuring lines in a region of interest in the radiograph of the sample bone; and processing the pattern or the patterns by arithmetic operations only in a predetermined local region equally extending on opposite sides of the middle of the bone width of said sample bone and corresponding to a cancellate bone.

17. The bone morphometric method according to claim 16, wherein said method further comprises the steps of:

measuring the sample bone by irradiating a radiograph of the sample bone and a standard matter having gradate thickness formed on an X-ray film with light and detecting the quantity of light transmitted through the radiograph for image reading; and processing the pattern or the patterns by arithmetic operations by converting the pattern into data expressed by the thickness of the standard matter on the basis of the relation between the thickness of the standard matter and the quantity of the transmitted light determined on the basis of the radiograph formed on the X-ray film.

18. A bone morphometric apparatus using a radiograph of a sample bone formed by radiography, said bone morphometric apparatus comprising:

means for measuring a pattern or a plurality of patterns of the quantity of transmitted radiation transmitted through the sample bone along a single or a plurality of measuring lines; and means for processing the pattern or the plurality of patterns only in a predetermined local region equally extending on opposite sides of the middle of the bone width of said sample bone and corresponding to a cancellate bone.

19. The bone morphometric method using a radiograph of a sample bone to measure the sample bone, said bone morphometric method comprising the steps of:

(1) producing a plurality of smoothed patterns by measuring patterns of the quantity of transmitted radiation along a predetermined plurality of substantially different measuring lines in a region of interest in the radiograph of the sample bone to obtain groups of patterns of the quantity of transmitted radiation, smoothing the patterns of some of the groups by a pattern smoothing operation and repeating the pattern smoothing operation for other groups of patterns;

(2) obtaining a plurality of groups of parameters necessary for bone measurement by processing the plurality of smoothed patterns by predetermined arithmetic operations; and (3) processing the plurality of groups of parameters under the predetermined conditions to measure the sample bone, said step of processing including comparing each group of parameters with given standard values, eliminating the groups of parameters deviating from the standard values by given values from the standard values, and calculating the means of the parameters of the remaining groups of parameters.

20. The bone morphometric method according to claim 19, wherein said method further comprises the steps of:

measuring the sample bone by irradiating a radiograph of the sample bone and a standard matter having gradate thickness formed on an X-ray film, with light; and detecting the quantity of light transmitted through the radiograph for image reading, wherein the patterns of the quantity of transmitted radiation are density patterns of the radiograph of the sample bone, and the predetermined arithmetic operations include a converting operation for converting the smooth patterns into data represented by the thickness of the standard matter on the basis of the relationship between the thickness of the standard matter and the quantity of transmitted light determined on the basis of the radiograph formed on the X-ray film.

21. The bone morphometric apparatus using a radiograph of a sample bone, said bone morphometric apparatus comprising:

(1) means for producing a plurality of smoothed patterns by measuring patterns of the quantity of transmitted radiation along a plurality of predetermined substantially different measuring lines in a region of interest in the radiograph of the sample bone to obtain groups of patterns of the quantity of transmitted radiation, smoothing patterns of some of the groups of patterns by a pattern smoothing operation, and repeating the pattern smoothing operation for other groups of patterns;

(2) means for obtaining a plurality of groups of parameters necessary for bone measurement by processing the plurality of smoothed patterns by predetermined arithmetic operations; and (3) means for processing the plurality of groups of parameters under the predetermined conditions to measure the sample bone, said step of processing including comparing each group of parameters with given standard values, eliminating the groups of parameters deviating from the standard values by given values from the standard values, and calculating the means of the parameters of the remaining groups of parameters.

22. A bone morphometric method comprising the steps of:

providing an image based on the quantity of transmitted radiation determined by irradiating a sample bone with radiation;

producing a pattern of the quantity of radiation transmitted through a region of interest along a measuring line in the region of interest in the input image;

specifying at least one of two boundary points on the boundary between osteocyte and soft tissues on the opposite ends of the sample bone in the pattern;

producing a corrected pattern representing the quantity of radiation transmitted through the sample bone proper by subtracting a pattern of the quantity of transmitted radiation transmitted through the soft tissues approximated by a line interconnecting the two boundary points from the pattern of the quantity of transmitted radiation transmitted through the region of interest; and processing the corrected pattern by arithmetic operations to measured the sample bone;

wherein the step of specifying at least one of the two boundary points comprises:

determining a first neighborhood point in the pattern;

determining an internal first regression line in a given range (2) skipping by a given range (1) from the first neighborhood point toward the center of the sample bone;

determining an external first regression line in a given range (4) skipping by a given range (3) from the first neighborhood point away from the center of the sample bone; and determining a second neighborhood point at the intersection of the inner first regression line and the outer first regression line and repeating the foregoing steps at least once until a new neighborhood point, meeting given conditions, is determined.

23. A bone morphometric apparatus comprising:

an image input means for providing an image representing the quantity of transmitted radiation determined by irradiating a sample bone with radiation and detecting the radiation transmitted through the sample bone;

means for producing a pattern of the quantity of radiation transmitted through a region of interest in the input image along a measuring line in the region of interest;

means for producing a corrected pattern representing the quantity of radiation transmitted through the sample bone proper by determining a first neighborhood point in the pattern, determining an internal regression line in a given range (2) slipping by a given range (1) from the first neighborhood point toward the center of the sample bone, determining an external regression line in a given range (4) by skipping by a given range (3) from the first neighborhood point away from the center of the sample bone, determining a second neighborhood point at the intersection of the inner first regression line and the external first regression line and repeating the foregoing steps until a new neighborhood point meets given conditions, to specify two boundary points on the boundary between the osteocyte and the soft tissue at the opposite ends of the sample bone in the pattern, and subtracting a pattern of the quantity of radiation transmitted through the soft tissues approximated by a line interconnecting the two boundary points from the pattern; and arithmetic means for processing the corrected pattern by arithmetic operations to measure the sample bone.

* * * * *